(12) United States Patent
Funaya et al.

(10) Patent No.: US 7,834,204 B2
(45) Date of Patent: Nov. 16, 2010

(54) FLUORENE DERIVATIVE, TRANSITION METAL COMPOUND, CATALYST FOR OLEFIN POLYMERIZATION, AND PROCESS FOR PRODUCING OLEFIN POLYMER

(75) Inventors: Munehito Funaya, Ichihara (JP); Koji Endo, Ichihara (JP); Naritoshi Hirota, Takaishi (JP); Yuichi Yamamura, Pittsburgh, PA (US); Koji Kawai, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 428 days.

(21) Appl. No.: 11/920,767

(22) PCT Filed: May 24, 2006

(86) PCT No.: PCT/JP2006/310391
§ 371 (c)(1),
(2), (4) Date: Nov. 20, 2007

(87) PCT Pub. No.: WO2006/126608
PCT Pub. Date: Nov. 30, 2006

(65) Prior Publication Data
US 2009/0253876 A1 Oct. 8, 2009

(30) Foreign Application Priority Data
May 25, 2005 (JP) .............................. 2005-152873

(51) Int. Cl.
C07F 17/00 (2006.01)
B01J 31/22 (2006.01)
C08F 4/6592 (2006.01)
(52) U.S. Cl. ......................................... 556/53; 502/152
(58) Field of Classification Search ................... 556/53; 502/152
See application file for complete search history.

(56) References Cited
U.S. PATENT DOCUMENTS
5,036,034 A 7/1991 Ewen
(Continued)

FOREIGN PATENT DOCUMENTS
EP 1 304 319 A2 4/2003
(Continued)

OTHER PUBLICATIONS

J.A. Ewen et al., "Syndiospecific Propylene Polymerizations with Group 4 Metallocenes," Journal of the American Chemical Society, vol. 110 (1988), pp. 6255-6256.

W. Kaminsky et al., "Polymerization of Propene and Butene with a Chiral Zirconocene and Methylalumoxane as Cocatalyst," Angewandte Chemie, vol. 24, No. 6, (1985), pp. 507-508.

S. Miller et al., "Isotactic—Hemiisotactic Polypropylene from $C_1$-Symmetric ansa-Metallocene Catalysts: A New Strategy for the Synthesis of Elastomeric Polypropylene," Organometallics, vol. 21, No. 5, Mar. 4, 2002, pp. 934-945.

Erik W. Thulstrup et al., "Orientation and linear dichroism of symmetrical aromatic molecules imbedded in stretched polyethylene", Journal of the American Chemical Society, vol. 104, No. 21, (1982), pp. 5594-5604.

Michele Regimbald-Krnel et al., "On the Di-1-naphthylcarbene-Dibenzofluorene Rearragement and the Ethylenization of Diarylcarbinols", Journal of Organic Chemistry, vol. 63, No. 23, (1998), pp. 8417-8423.

Search Report mailed Jun. 8, 2009 in corresponding Singapore Application No. 200718075-5.

Primary Examiner—Caixia Lu
(74) Attorney, Agent, or Firm—Foley & Lardner LLP

(57) ABSTRACT

Provided is a transition metal compound represented by the general formula [III]:

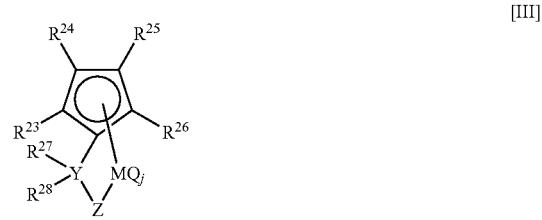

wherein $R^{23}$, $R^{24}$, $R^{25}$, $R^{26}$, $R^{27}$, and $R^{28}$ are each independently selected from hydrogen, a hydrocarbon group, a silicon-containing group, a sulfur-containing group, an oxygen-containing group, a nitrogen-containing group, and a halogen-containing group, adjacent substituents of $R^{23}$ to $R^{28}$ are optionally bonded to each other to form a ring, M is a Group 4 transition metal, Y is carbon atom, Q is selected from halogen, a hydrocarbon group, an anionic ligand and a neutral ligand capable of coordinating with a lone electron pair, which is selected in the same combination or different combination, j is an integer of 1 to 4, and Z is a fluorenylidene group comprising a fluorene derivative formula [I] or formula [II]

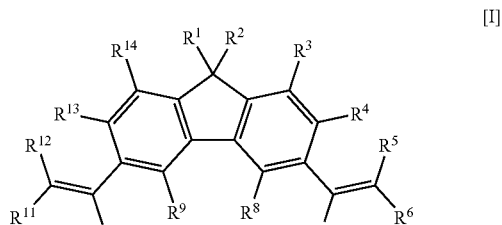

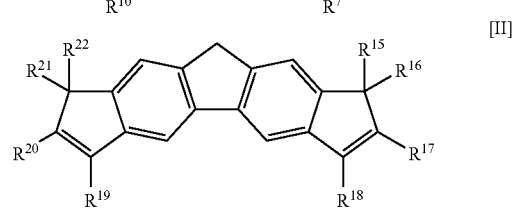

6 Claims, No Drawings

U.S. PATENT DOCUMENTS

| | | |
|---|---|---|
| 5,416,228 A | 5/1995 | Ewen et al. |
| 5,565,592 A | 10/1996 | Patsidis et al. |
| 5,616,752 A | 4/1997 | Patsidis et al. |
| 5,710,224 A | 1/1998 | Alt et al. |
| 5,731,254 A | 3/1998 | Winter et al. |
| 6,316,558 B1 | 11/2001 | Kaneko et al. |
| 6,369,175 B1 | 4/2002 | Ewen |
| 6,559,089 B1 | 5/2003 | Razavi et al. |
| 6,939,928 B1 | 9/2005 | Kawai et al. |
| 2003/0143422 A1 | 7/2003 | Chen |

FOREIGN PATENT DOCUMENTS

| | | |
|---|---|---|
| JP | 2-274703 A | 11/1990 |
| JP | 3-193796 A | 8/1991 |
| JP | 6-122718 A | 5/1994 |
| JP | 9-240149 | 9/1997 |
| JP | 10-226694 A | 8/1998 |
| JP | 11-228588 A | 8/1999 |
| JP | 2001-526730 A | 12/2001 |
| JP | 2003-49044 | 2/2003 |
| JP | 2005-513713 A | 5/2005 |
| WO | WO 01/27124 A1 | 4/2001 |

FLUORENE DERIVATIVE, TRANSITION METAL COMPOUND, CATALYST FOR OLEFIN POLYMERIZATION, AND PROCESS FOR PRODUCING OLEFIN POLYMER

TECHNICAL FIELD

The present invention relates to a transition metal compound which is useful as a catalyst component for olefin polymerization and has a novel specific structure, an intermediate which is useful in the production of the transition metal compound, a catalyst for olefin polymerization containing the transition metal compound, and a process for producing an olefin polymer using the catalyst.

BACKGROUND ART

In recent years, a metallocene compound has been well known as a homogeneous catalyst for olefin polymerization. Many studies have been extensively carried out on a process for polymerizing an olefin with the use of a metallocene compound, especially on a process for stereoregularly polymerizing an olefin, since the report on an isotactic polymerization by W. Kaminsky et al (Angew. Chem. Int. Ed. Engl., 24,507 (1985)) has been published.

It has been known that in the polymerization of an α-olefin using a metallocene compound, the stereoregularity and the molecular weight of the obtained α-olefin polymer vary markedly by introducing a substituent on a cyclopentadienyl ring of the ligand of a metallocene compound, or bridging two cyclopentadienyl rings.

For example, there has been disclosed that when a metallocene compound having a ligand in which a cyclopentadienyl ring and a fluorenyl ring are bridged is used as a propylene polymerization catalyst, from the view point of the stereoregularity, syndioctactic polypropylene is obtained in the case of using dimethylmethylene (cyclopentadienyl) (fluorenyl)zirconium dichloride (J. Am. Chem. Soc., 110, 6255 (1988)); hemiisotactic polypropylene is obtained in the case of dimethylmethylene(3-methylcyclopentadienyl)(fluorenyl)zirconium dichloride in which a methyl group is introduced at the 3-position of a cyclopentadienyl ring [Japanese Unexamined Patent Application Publication No. H3-193796]; and isotactic polypropylene is obtained in the case of dimethylmethylene(3-tert butylcyclopentadienyl) (fluorenyl)zirconium dichloride in which a tert-butyl group is similarly introduced [Japanese Unexamined Patent Application Publication No. H6-122718]. In addition, there has been disclosed that polypropylene with improved isotactic stereoregularity is obtained in the case of using dimethylmethylene (3-tert-butyl-5-methylcyclopentadienyl)(3,6-di-tert-butylfluorenyl)zirconium dichloride in which a tert-butyl group is introduced at the 3- and 6-positions of a fluorenyl ring, as compared with the case of using dimethylmethylene(3-tert-butyl-5-methylcyclopentadienyl)(fluorenyl)zirconium dichloride (WO01/27124).

Moreover, there has been disclosed that, from the view point of the molecular weight, syndiotactic polypropylene having a higher molecular weight is obtained in the case of using diphenylmethylene(cyclopentadienyl)(fluorenyl)zirconium dichloride in which a bridging part of a cyclopentadienyl ring and a fluorenyl ring is replaced with a diphenylmethylene bridge, as compared with the case of using dimethylmethylene(cyclopentadienyl)(fluorenyl)zirconium dichloride (Japanese Unexamined Patent Application Publication No. H2-274703); isotactic-hemiisotactic polypropylene having a higher molecular weight is obtained in the case of using diphenylmethylene(3-(2-adamantyl)cyclopentadienyl)(fluorenyl)zirconium dichloride in which a bridging part is replaced with a diphenylmethylene bridge, as compared with the case of using dimethylmethylene(3-(2-adamantyl) cyclopentadienyl)(fluorenyl)zirconium dichloride (Organometallics, 21, 934 (2002)); and isotactic polypropylene having a higher molecular weight is obtained in the case of using dimethylmethylene(3-tert-butyl-5-methylcyclopentadienyl) (fluorenyl)zirconium dichloride in which a methyl group is also introduced at the 5-position of a cyclopentadienyl ring, as compared with the case of using dimethylmethylene(3-tert-butylcyclopentadienyl)(fluorenyl)zirconium dichloride (PCT Japanese Translation Patent Publication No. 2001-526730), respectively.

Furthermore, there has been disclosed that, with the use of dimethylmethylene(3-tert-butyl-2-methylcyclopentadienyl) (fluorenyl)zirconium dichloride and diphenylmethylene(3,4-dimethylcyclopentadienyl)(fluorenyl)zirconium dichloride, in which substituents are introduced at two adjacent positions of a cyclopentadienyl ring, polypropylene having a lower molecular weight is obtained, as compared with that prepared with the use of dimethylmethylene(3-tert-butyl-5-methylcyclopentadienyl)(fluorenyl)zirconium dichloride and diphenylmethylene(3-methylcyclopentadienyl)(fluorenyl)zirconium dichloride, respectively (PCT Japanese Translation Patent Publication No. 2001-526730, and Japanese Unexamined Patent Application Publication No. H10-226694).

As described above, there have been many examples of reports on the metallocene compound having a ligand in which a cyclopentadienyl ring and a fluorenyl ring are bridged. On the other hand, as for the kinds of the substituent at the 3- and 6-positions of a fluorene ring, the reported examples have been extremely limited. Specifically, a metallocene compound in which a tert-butyl group is substituted at the 3- and 6-positions of a fluorene ring, and a metallocene compound in which the 2- and 3-positions, and the 6- and 7-positions of a fluorene ring form a saturated 6-membered ring have been known (WO01/27124), but there has been no reported examples of the synthesis and polymerization of a metallocene compound having a fluorene ring in which an unsaturated bond is substituted at the 3- and 6-positions. In addition, there has been no reported examples of the synthesis of a fluorene derivative in which a carbon-carbon unsaturated bond is substituted at the 3- and 6-positions. Thus, the performances of such metallocene compound have not been yet known.

Generally, there is a need for improvement of a polymerization catalyst with the use of these metallocene compounds from the view point of the polymerization activity, the stereoregularity, the molecular weight, or the like.

On the other hand, in recent years, since a fluorene compound has been used as an organic electroluminescence element, production of fluorene in which an unsaturated bond is substituted at the 3 and 6-positions, is also useful in these field.

[Patent Document 1] Japanese Unexamined Patent Application Publication No. H3-193796

[Patent Document 2] Japanese Unexamined Patent Application Publication No. H6-122718

[Patent Document 3] WO 01/27124

[Patent Document 4] Japanese Unexamined Patent Application Publication No. H2-274703

[Patent Document 5] PCT Japanese Translation Patent Publication No. 2001-526730

[Patent Document 6] Japanese Unexamined Patent Application Publication No. H10-226694

[Non-Patent Document 1] Angew. Chem. Int. Ed. Engl., 24,507 (1985)

[Non-Patent Document 2] J. Am. Chem. Soc., 110, 6255 (1988)

[Non-Patent Document 3] Organometallics, 21, 934 (2002)

DISCLOSURE OF THE INVENTION

Problem to be Solved by the Invention

It is an object of the present invention to provide a novel fluorene compound which is useful as an organic electroluminescence element, and an intermediate of a transition metal compound for olefin polymerization, a transition metal compound containing a fluorene ring in its partial structure as a catalyst component for olefin polymerization, a catalyst for olefin polymerization containing the transition metal compound, and a process for producing an olefin polymer using the catalyst.

Means for Solving the Problem

The present invention was made in order to solve the above-mentioned problems, and as a result, the present object is achieved by a fluorene compound in which an unsaturated bond is substituted at the 3- and 6-positions, a useful and novel transition metal compound having a ligand containing the fluorene compound, a catalyst for olefin polymerization containing the transition metal compound, and a process for producing an olefin polymer using the catalyst for polymerization, thereby completing the invention. The fluorene and the transition metal compound according to the invention are the transition metal compounds represented by the following general formula [I] and [III], respectively.

[a]: A fluorene derivative represented by the following general formula [I]:

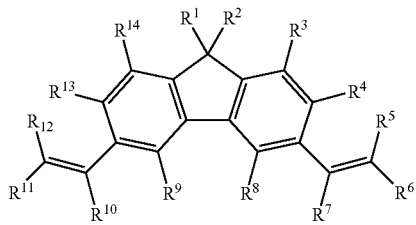

wherein $R^1$, $R^2$, $R^3$, $R^5$, $R^6$, $R^7$, $R^8$, $R^9$, $R^{10}$, $R^{11}$, $R^{12}$, and $R^{14}$ are each selected from hydrogen, a hydrocarbon group, and a silicon-containing group, and may be the same as or different from each other, $R^4$ and $R^{13}$ are each selected from hydrogen, a hydrocarbon group, a silicon-containing group, a sulfur-containing group, an oxygen-containing group, a nitrogen-containing group, and a halogen-containing group, and may be the same as or different from each other, adjacent substituents of $R^1$ to $R^{14}$ may be bonded to each other to form a ring, $R^4$ and $R^5$ may be joined together to form -Ra- which is divalent, $R^{12}$ and $R^{13}$ may be joined together to form -Rb- which is divalent, and Ra and Rb are each a divalent substituent other than a vinylene group, which is selected from a hydrocarbon group, a silicon-containing group, a sulfur-containing group, an oxygen-containing group, a nitrogen-containing group, and a halogen-containing group.

[b]: The fluorene derivative as described in [a], in which $R^1$ and $R^2$ are each hydrogen in the above general formula [I].

[c]: The fluorene derivative as described in [b], in which $R^1$, $R^2$, $R^3$, $R^8$, $R^9$, and $R^{14}$ are each hydrogen in the above general formula [I].

[d]: The fluorene derivative as described in [c], in which $R^1$, $R^2$, $R^3$, $R^8$, $R^9$, and $R^{14}$ are each hydrogen, and $R^4$ and $R^5$ and/or $R^{12}$ and $R^{13}$ are bonded to each other to form a ring in the above general formula [I].

[e]: The fluorene derivative as described in [d], in which $R^1$, $R^2$, $R^3$, $R^8$, $R^9$, and $R^{14}$ are each hydrogen, and $R^4$ and $R^5$ and/or $R^{12}$ and $R^{13}$ are bonded to each other to form a 5- or 6-membered ring in the above general formula [I].

[f]: The fluorene derivative as described in [e] represented by the following general formula [II]:

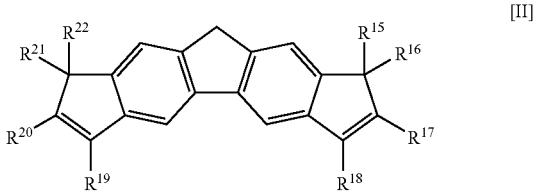

wherein $R^{15}$, $R^{16}$, $R^{17}$, $R^{18}$, $R^{19}$, $R^{20}$, $R^{21}$, and $R^{22}$ are each selected from hydrogen, a hydrocarbon group, a silicon-containing group, a sulfur-containing group, an oxygen-containing group, a nitrogen-containing group, and a halogen-containing group, and may be the same as or different from each other.

[g]: The fluorene derivative as described in [f], in which $R^{15}$, $R^{16}$, $R^{18}$, $R^{19}$, $R^{21}$, and $R^{22}$ are each a methyl group, and $R^{17}$ and $R^{20}$ are each hydrogen in the above general formula [II].

[h]: A transition metal compound represented by the following general formula [III]:

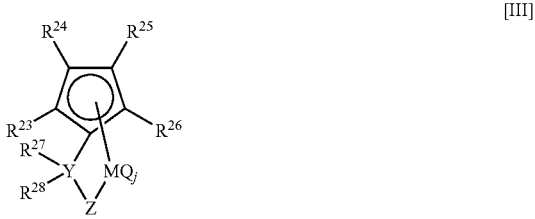

wherein $R^{23}$, $R^{24}$, $R^{25}$, $R^{26}$, $R^{27}$, and $R^{28}$ are each selected from hydrogen, a hydrocarbon group, a silicon-containing group, a sulfur-containing group, an oxygen-containing group, a nitrogen-containing group, and a halogen-containing group, and may be the same as or different from each other, adjacent substituents of $R^{23}$ to $R^{28}$ may be bonded to each other to form a ring, M is a Group 4 transition metal, Y is carbon atom, Q may be selected from halogen, a hydrocarbon group, an anionic ligand and a neutral ligand capable of coordinating with a lone electron pair, which may be selected in the same combination or different combination, j is an integer of 1 to 4, and Z is a fluorenylidene group having a free valency of divalence, which is derived by removing $R^1$ and $R^2$ from the fluorene derivative as described in [a] to [e] represented by the general formula [I] or a fluorenylidene group having a free valency of divalence, which is derived by removing two hydrogen atoms at the 10-position of the fluorene derivative as described in [f] of [g]. In the present invention, the term "the 10-position of the fluorene derivative"

indicates the position represented by * in the following diagram. In the diagram, description of chemical bond neighboring parts beyond double wavy line of the fluorene skeleton is abbreviated.

[i]: The transition metal compound as described in [h], in which $R^{24}$ and $R^{26}$ are each hydrogen in the above general formula [III].

[j]: A catalyst for olefin polymerization comprising the transition metal compound as described in [h] or [i].

[k]: A catalyst for olefin polymerization comprising:
(A) the transition metal compound as describe in [h] or [j]; and
(B) at least one compound selected from;
(B-1) an organometallic compound,
(B-2) an organoaluminum oxy-compound, and
(B-3) a compound which forms an ion pair by reacting with the transition metal compound (A).

[1]: A process for producing an olefin polymer comprising polymerizing one or more monomer selected from ethylene and an α-olefin, in the presence of the catalyst for olefin polymerization as described in [j] or [k], in which at least one monomer is ethylene or propylene.

[m]: The process for producing an olefin polymer as described in [1], in which the transition metal compound represented by the general formula [II] is used in a form of supported on a support.

Effect of the Invention

A method of producing a useful olefin polymer with high activity can be provided by using a novel fluorene derivative, a transition metal compound (metallocene compound) containing the derivative, and a catalyst for olefin polymerization containing the transition metal compound, of the present invention.

BEST MODE FOR CARRYING OUT THE INVENTION

Hereinafter, a fluorene derivative represented by the above-mentioned formula [I], a transition metal compound represented by the above-mentioned formula [III], a preferred fluorene derivative, and a preferred transition metal compound will be exemplified, and further a process for producing the fluorene derivative of the invention, a process for producing the transition metal compound of the invention, a preferred embodiment of employing the transition metal compound of the invention for a catalyst for olefin polymerization, and a process for producing an olefin polymer in the presence of the catalyst for olefin polymerization containing the transition metal compound of the invention will be explained one after another.

Fluorene Derivative

The fluorene derivative of the present invention is represented by the general formula [I]. In the general formula [I], $R^1, R^2, R^3, R^5, R^6, R^7, R^8, R^9, R^{10}, R^{11}, R^{12}$, and $R^{14}$ are each selected from hydrogen, a hydrocarbon group, a silicon-containing group, a sulfur-containing group, an oxygen-containing group, a nitrogen-containing group, and a halogen-containing group, and may be the same as or different from each other. Examples of the hydrocarbon group include a linear chain hydrocarbon group such as a methyl group, an ethyl group, an n-propyl group, an allyl group, an n-butyl group, an n-pentyl group, an n-hexyl group, an n-heptyl group, an n-octyl group, an n-nonyl group, and an n-decanyl group; a branched hydrocarbon group such as an isopropyl group, a tert-butyl group, an amyl group, a 3-methylpentyl group, a 1,1-diethylpropyl group, a 1,1-dimethylbutyl group, a 1-methyl-1-propylbutyl group, a 1,1-propylbutyl group, a 1,1-dimethyl-2-methylpropyl group, and a 1-methyl-1-isopropyl-2-methylpropyl group; a cyclic saturated hydrocarbon group such as a cyclopentyl group, a cyclohexyl group, a cycloheptyl group, a cyclooctyl group, a norbornyl group, an adamantyl group, a methylcyclohexyl group, and a methyladamantyl group; a cyclic unsaturated hydrocarbon group such as a phenyl group, a tolyl group, a naphthyl group, a biphenyl group, a phenanthryl group, an anthracenyl group; a saturated hydrocarbon group substituted with a cyclic unsaturated hydrocarbon group such as a benzyl group, a cumyl group, a 1,1-diphenylethyl group, and a triphenylmethyl group. Examples of the oxygen-containing group include a methoxy group, an ethoxy group, a phenoxy group, and a furyl group. Examples of the nitrogen-containing group include an N-methylamino group, an N,N-dimethylamino group, an N-phenylamino group, and a pyryl group. Examples of the sulfur-containing group include a methylthio group and a thienyl group. Examples of the silicon-containing group include a trimethylsilyl group, a triethylsilyl group, a dimethylphenylsilyl group, a diphenylmethylsilyl group, and a triphenylsilyl group. Examples of the halogen-containing group include a fluorine atom, a fluorine-containing group such as a trifluoromethyl group, a 2,2,2-trifluoroethyl group, a fluorophenyl group, a difluorophenyl group, a trifluorophenyl group, a pentafluorophenyl group, a trifluoromethylphenyl group, and bis(trifluoromethyl group), a chlorine atom, a chlorine-containing group such as a trichloromethyl group, a 2,2,2-trichloroethyl group, a chlorophenyl group, a dichlorophenyl group, a trichlorophenyl group, a pentachlorophenyl group, a trichloromethylphenyl group, and bis(trichloromethyl group), a bromine atom, a bromine-containing group such as a bromophenyl group, an iodine atom, and an iodine-containing group such as an iodophenyl group.

In the general formula [I], $R^1, R^2, R^3, R^5, R^6, R^7, R^8, R^9, R^{10}, R^{11}, R^{12}$, and $R^{14}$ are each preferably hydrogen, a hydrocarbon group having 1 to 20 carbon atom(s), a silicon-containing group having 0 to 20 carbon atom(s), a sulfur-containing group, an oxygen-containing group, a nitrogen-containing group, and a halogen-containing group. As the hydrocarbon group having 1 to 20 carbon atom(s), the silicon-containing group having 0 to 20 carbon atom(s), the sulfur-containing group, the oxygen-containing group, the nitrogen-containing group, and the halogen-containing group, the above-mentioned substituent may be exemplified.

In addition, adjacent substituents of $R^1$ to $R^{14}$ may be bonded to each other to form a ring, and may be joined together to form a ring having 1 to 20 carbon atom(s), in which an oxygen atom, a nitrogen atom, and a sulfur atom may be contained, together with the atom which connects the adjacent substituents. Furthermore, $R^4$ and $R^5$ may be joined together to form Ra which is divalent, $R^{12}$ and $R^{13}$ may be joined together to form Rb which is divalent. Ra and Rb are each a divalent substituent other than a vinylene group, which is preferably a hydrocarbon group having 1 to 20 carbon atom(s), a silicon-containing group having 0 to 20 carbon atom(s), a sulfur-containing group, an oxygen-containing group, a nitrogen-containing group, and a halogen-containing group. Examples of the hydrocarbon group of divalent include a methylene group, an ethylene group, an ethylidene group, a propylene group, an isopropylidene group, a dimethylethylene group, a trimethylethylene group, a tetramethylethylene group, a trimethylene group, a trimethyltrimethylene group, a hexamethyltrimethylene group, a tetramethylene group, an octamethyltetramethylene group, a propenylene group, avinylidene group, a cyclohexylidene group, and a 1,2-cyclohexenylene group. Examples of the silicon-containing group include a silylene group, a dimethylsilylene group, a disilene group, tetramethyldisilene group, a silaethylene group, a dimethylsilaethylene group, and tetramethylsilaethylene group. Examples of the sulfur-containing group include a sulfur atom, a thiaethylene group, a dimethylthiaethylene group, and a thioxomethylene group. Examples of the oxygen-containing group include an oxygen atom, an oxaethylene group, a dimethyloxaethylene group, and an oxomethylene group. Examples of the nitrogen-containing group include an imino group, a methylimino group, a phenylimino group, an azaethylene group, an N-methylazaethylene group, an N-phenylazaethylene group, a trimethylazaethylene group, an iminomethylene group, and an N-methyliminomethylene group. Examples of halogen-containing group include a fluoromethylene group, a difluoromethylene group, a (trifluoromethyl)methylene group, a bis(trifluoromethyl)methylene group, a tetrafluoroethylene group, a chloromethylene group, a dichloromethylene group, a dibromomethylene group, and a diiodomethylene group.

Specific examples of the fluorene derivative in which such adjacent substituents form a ring include the compounds represented by the following formula [II].

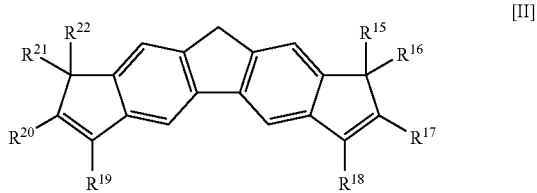

[II]

In the general formula [II], $R^{15}$, $R^{16}$, $R^{17}$, $R^{18}$, $R^{19}$, $R^{20}$, $R^{21}$, and $R^{22}$ are each selected from hydrogen, a hydrocarbon group, a silicon-containing group, a sulfur-containing group, an oxygen-containing group, a nitrogen-containing group, and a halogen-containing group, and may be the same as or different from each other. $R^{15}$, $R^{16}$, $R^{17}$, $R^{18}$, $R^{19}$, $R^{20}$, $R^{21}$, and $R^{22}$ are each preferably a hydrogen atom, a hydrocarbon group having 1 to 20 carbon atom(s), a silicon-containing group having 0 to 20 carbon atom(s), a sulfur-containing group, an oxygen-containing group, and a nitrogen-containing group. As the hydrocarbon group having 1 to 20 carbon atom(s), the silicon-containing group having 0 to 20 carbon atom(s), the sulfur-containing group, the oxygen-containing group, the nitrogen-containing group, and the halogen-containing group, the above-mentioned substituent may be exemplified, which is more preferably a hydrogen atom, or a hydrocarbon group having 1 to 20 carbon atom(s), and particularly preferably hydrogen or a methyl group.

Transition Metal Compound

The transition metal compound of the present invention is represented by the general formula [III]. In the general formula [III], $R^{23}$, $R^{24}$, $R^{25}$, $R^{26}$, $R^{27}$, and $R^{28}$ are each selected from hydrogen, a hydrocarbon group, a silicon-containing group, a sulfur-containing group, an oxygen-containing group, a nitrogen-containing group, and a halogen-containing group, and may be the same as or different from each other, adjacent substituents of $R^{23}$ to $R^{28}$ may be bonded to each other to form a ring. M is a Group 4 transition metal, Y is carbon atom, Q may be selected from halogen, a hydrocarbon group, an anionic ligand and a neutral ligand capable of coordinating with a lone electron pair, which may be selected in the same combination or different combination, and j is an integer of 1 to 4. Z is a fluorenylidene group comprising the above-mentioned fluorene derivative.

Examples of the hydrocarbon group include a linear chain hydrocarbon group such as a methyl group, an ethyl group, an n-propyl group, an allyl group, an n-butyl group, an n-pentyl group, an n-hexyl group, an n-heptyl group, an n-octyl group, an n-nonyl group, and an n-decanyl group; a branched hydrocarbon group such as an isopropyl group, a tert-butyl group, an amyl group, a 3-methylpentyl group, a 1,1-diethylpropyl group, a 1,1-dimethylbutyl group, a 1-methyl-1-propylbutyl group, a 1,1-propylbutyl group, a 1,1-dimethyl-2-methylpropyl group, and a 1-methyl-1-isopropyl-2-methylpropyl group; a cyclic saturated hydrocarbon group such as a cyclopentyl group, a cyclohexyl group, a cycloheptyl group, a cyclooctyl group, a norbornyl group, an adamantyl group, a methylcyclohexyl group, and a methyladamantyl group; a cyclic unsaturated hydrocarbon group such as a phenyl group, a tolyl group, a naphthyl group, a biphenyl group, a phenanthryl group, an anthracenyl group; a saturated hydrocarbon group substituted with a cyclic unsaturated hydrocarbon group such as a benzyl group, a cumyl group, a 1,1-diphenylethyl group, and a triphenylmethyl group. Examples of the oxygen-containing group include a methoxy group, an ethoxy group, a phenoxy group, and a furyl group. Examples of the nitrogen-containing group include an N-methylamino group, an N,N-dimethylamino group, an N-phenylamino group, and a pyrrolyl group. Examples of the sulfur-containing group include a methylthio group and a thienyl group. Examples of the silicon-containing group include a trimethylsilyl group, a triethylsilyl group, a dimethylphenylsilyl group, a diphenylmethylsilyl group, and a triphenylsilyl group. Examples of the halogen-containing group include a fluorine atom, a fluorine-containing group such as a trifluoromethyl group, a 2,2,2-trifluoroethyl group, a fluorophenyl group, a difluorophenyl group, a trifluorophenyl group, a pentafluorophenyl group, a trifluoromethylphenyl group, and bis(trifluoromethyl group), a chlorine atom, a chlorine-containing group such as a trichloromethyl group, a 2,2,2-trichloroethyl group, a chlorophenyl group, a dichlorophenyl group, a trichlorophenyl group, a pentachlorophenyl group, a trichloromethylphenyl group, and bis(trichloromethyl group), a bromine atom, a bromine-containing group such as a bromophenyl group, an iodine atom, and an iodine-containing group such as an iodophenyl group.

In the general formula [III], $R^{23}$, $R^{24}$, $R^{25}$, and $R^{26}$, which are substituents on a cyclopentadienyl ring, each is preferably hydrogen or a hydrocarbon group having 1 to 20 carbon atom(s). As the hydrocarbon group having 1 to 20 carbon atom(s), the above-mentioned hydrocarbon group may be exemplified. It is more preferred that $R^{24}$, $R^{26}$ are each hydrogen. It is even more preferred that $R^{23}$ and/or $R^{25}$ are/is a hydrocarbon group having 1 to 20 carbon atom(s). As the hydrocarbon group having 1 to 20 carbon atom(s), the above-mentioned hydrocarbon group may be exemplified.

In the above-mentioned general formula [I], Y bridging a cyclopentadienyl ring and a fluorenyl ring is a carbon atom. $R^{27}$ and $R^{28}$, which are substituents at Y, are each preferably hydrogen, a hydrocarbon group having 1 to 20 carbon atom(s), a silicon-containing group having 0 to 20 carbon atom(s), a sulfur-containing group, an oxygen-containing group, a nitrogen-containing group, or a halogen-containing group. Examples of the hydrocarbon group having 1 to 20 carbon atom(s), the silicon-containing group having 0 to 20 carbon atom(s), the sulfur-containing group, the oxygen-containing group, the nitrogen-containing group, and the halogen-containing group include the substituent as mentioned above. These may be the same as or different from each other, and may be bonded to form a ring. Examples of the substituent, with which $R^{13}$ and $R^{14}$ are bonded to each other to form a ring, include a cyclopentylidene group, a cyclohexylidene group, a cycloheptylidene group, a fluorenylidene group, a 10-hydroanthracenylidene group, and a dibenzocycloheptadienylidene group.

In the above-mentioned general formula [III], M is a Group 4 transition metal, specifically Ti, Zr, or Hf. Q may be selected from halogen, a hydrocarbon group, an anionic ligand and a neutral ligand capable of coordinating with a lone electron pair, which may be selected in the same combination or different combination. j is an integer of 1 to 4, wherein when j is 2 or more, Q may be the same as or different from each other. Specific examples of the halogen atom include a fluorine atom, a chlorine atom, a bromine atom and an iodine atom, and specific examples of the hydrocarbon group may be the same one as exemplified above. Specific examples of the anionic ligand include an alkoxy group such as methoxy, tert-butoxy and phenoxy; a carboxylate group such as acetate and benzoate; a sulfonate group such as mesylate and tosilate; an amide group such as dimethylamide, diisopropylamide, methylanilide, and diphenylamide. Specific examples of the neutral ligand capable of coordinating with a lone electron pair include an organic phosphorous compound such as trimethyl phosphine, triethyl phosphine, triphenyl phosphine and diphenyl methyl phosphine; ethers such as tetrahydrofuran, diethylether, dioxane and 1,2-dimethoxyethan; and the like. It is preferable that at least one of Q is halogen or an alkyl group.

Examples of Preferred Fluorene Derivative

Examples of preferred fluorene derivative include 1,1,3,6,8,8-hexamethyl-1H,8H-dicyclopenta[b,h]fluorene, 1,1,8,8-tetramethyl-1H,8H-dicyclopenta[b,h]fluorene, 1,3,6,8-tetramethyl-1H,8H-dicyclopenta[b,h]fluorene, 3,6-dimethyl-1H,8H-dicyclopenta[b,h]fluorene, 1H,8H-dicyclopenta[b,h]fluorene, 1,1,3-trimethyl-1H-cyclopenta[b]fluorene, 1,3-dimethyl-1H-cyclopenta[b]fluorene, 1,1-dimethyl-1H-cyclopenta[b]fluorenylfluorene, 1-methyl-1H-cyclopenta[b]fluorene, 3-methyl-1H-cyclopenta[b]fluorene, 2,7-dimethyl-1H,8H-dicyclopenta[b,h]fluorene, 2-methyl-1H,8H-dicyclopenta[b,h]fluorene, 1,1,2,3,6,7,8,8-octamethyl-1H,8H-dicyclopenta[b,h]fluorene, 1,1,2,7,8,8-hexamethyl-1H,8H-dicyclopenta[b,h]fluorene, 3,6-diisopropyl-1,1,8,8-tetramethyl-1H,8H-dicyclopenta[b,h]fluorene, 3,6-diisopropyl-1H,8H-dicyclopenta[b,h]fluorene, 3,6-diisopropyl-1,3-dimethyl-1H-cyclopenta[b]fluorene, 3-isopropyl-1,1-dimethyl-1H-cyclopenta[b]fluorene, 3-isopropyl-1-methyl-1H-cyclopenta[b]fluorene, 3,6-diisopropyl-2,7-dimethyl-1H,8H-dicyclopenta[b,h]fluorene, 3,6-diisopropyl-2-methyl-1H,8H-dicyclopenta[b,h]fluorene, 3,6-di-tert-butyl-1,1,2,7,8,8-hexamethyl-1H,8H-dicyclopenta[b,h]fluorene, 3,6-di-tert-butyl-1,1,8,8-tetramethyl-1H,8H-dicyclopenta[b,h]fluorene, 3,6-di-tert-butyl-1,3-dimethyl-1H-cyclopenta[b]fluorene, 3-tert-butyl-1,1-dimethyl-1H-cyclopenta[b]fluorene, 3-tert-butyl-1-methyl-1H-cyclopenta[b]fluorene, 3,6-di-tert-butyl-2,7-dimethyl-1H,8H-dicyclopenta[b,h]fluorene, 3,6-di-tert-butyl-2-methyl-1H,8H-dicyclopenta[b,h]fluorene, 3,6-di-tert-butyl-1,1,2,7,8,8-hexamethyl-1H,8H-dicyclopenta[b,h]fluorene, 1,2,9,10-tetrahydro-dibenzo[b,h]fluorene, 1,1,10,10-tetramethyl-1,2,9,10-tetrahydro-dibenzo[b,h]fluorene, 1,10-dimethyl-1,2,9,10-tetrahydro-dibenzo[b,h]fluorene, 4,7-dimethyl-1,2,9,10-tetrahydro-dibenzo[b,h]fluorene, 1,1,4,7,10,10-hexamethyl-1,2,9,10-tetrahydro-dibenzo[b,h]fluorene, 1H,2H-benzo[b]fluorene, 1,1-dimethyl-1H,2H-benzo[b]fluorene, 1,1,4-trimethyl-1H,2H-benzo[b]fluorene, 1,4-dimethyl-1H,2H-benzo[b]fluorene, 4-methyl-1H,2H-benzo[b]fluorene, 4,7-di-tert-butyl-1,2,9,10-tetrahydro-dibenzo[b,h]fluorene, 4,7-di-tert-butyl-1,1,10,10-tetramethyl-1,2,9,10-tetrahydro-dibenzo[b,h]fluorene, 4,7-di-tert-butyl-1,10-dimethyl-1,2,9,10-tetrahydro-dibenzo[b,h]fluorene, 4-tert-butyl-1,1-dimethyl-1H,2H-benzo[b]fluorene, 4-tert-butyl-1-methyl-1H,2H-benzo[b]fluorene, 3,6-divinylfluorene, 3-vinylfluorene, 3,6-di-isopropenylfluorene, 3-isopropenylfluorene, 3,6-dipropenylfluorene, 3-propenylfluorene, 3,6-di-(2-methylisopropenyl)fluorene, 3-(2-methylisopropenyl)fluorene, 3,6-di-(2-phenylisopropenyl)fluorene, 3-(2-phenylisopropenyl)fluorene, 3,6-distyrylfluorene, 3-styrylfluorene, 3,6-di-(2-phenyl)propenylfluorene, 3-(2-phenyl)propenylfluorene, 3,6-di-(1-methyl-2-phenyl)propenylfluorene, and 3-(1-methyl-2-phenyl)propenylfluorene. However, the fluorene derivative of the present invention is not limited to the above-exemplified compounds, and examples thereof include all the compounds satisfying the requirements as described in the claims.

Examples of Preferred Transition Metal Compound

Examples of preferred transition metal compound include isopropylidene(cyclopentadienyl)(1,1,3,6,8,8-hexamethyl-1H,8H-dicyclopenta[b,h]fluorenyl)zirconium dichloride, dibutylmethylene(cyclopentadienyl)(1,1,3,6,8,8-hexamethyl-1H,8H-dicyclopenta[b,h]fluorenyl)zirconium dichloride, cyclohexylidene(cyclopentadienyl)(1,1,3,6,8,8-hexamethyl-1H,8H-dicyclopenta[b,h]fluorenyl)zirconium dichloride, dibenzylmethylene(cyclopentadienyl)(1,1,3,6,8,8-hexamethyl-1H,8H-dicyclopenta[b,h]fluorenyl)zirconium dichloride, phenylmethylene(cyclopentadienyl)(1,1,3,6,8,8-hexamethyl-1H,8H-dicyclopenta[b,h]fluorenyl)zirconium dichloride, (phenyl)(methyl)methylene(cyclopentadienyl)(1,1,3,6,8,8-hexamethyl-1H,8H-dicyclopenta[b,h]fluorenyl)zirconium dichloride, (p-tolyl)(methyl)methylene(cyclopentadienyl)(1,1,3,6,8,8-hexamethyl-1H,8H-dicyclopenta[b,h]fluorenyl)zirconium dichloride, (phenyl)(ethyl)methylene(cyclopentadienyl)(1,1,3,6,8,8-hexa methyl-1H,8H-dicyclopenta[b,h]fluorenyl)zirconium dichloride, diphenylmethylene(cyclopentadienyl)(1,1,3,6,8,8-hexamethyl-1H,8H-dicyclopenta[b,h]fluorenyl)zirconium dichloride, di-p-tolylmethylene(cyclopentadienyl)(1,1,3,6,8,8-hexamethyl-1H,8H-dicyclopenta[b,h]fluorenyl)zirconium dichloride, bis(p-trifluoromethylphenyl)methylene(cyclopentadienyl)(1,1,3,6,8,8-hexamethyl-1H,8H-dicyclopenta[b,h]fluorenyl)zirconium dichloride, bis(m-trifluoromethylphenyl)methylene(cyclopentadienyl)(1,1,3,6,8,8-hexamethyl-1H,8H-dicyclopenta[b,h]fluorenyl)zirconium dichloride, bis(p-fluorophenyl)methylene(cyclopentadienyl)(1,1,3,6,8,8-hexamethyl-1H,8H-dicyclopenta[b,h]fluorenyl)zirconium dichloride, bis(m-fluorophenyl)methylene(cyclopentadienyl)(1,1,3,6,8,8-hexamethyl-1H,8H-dicyclopenta[b,h]fluorenyl)zirconium dichloride, bis(p-chlorophenyl methylene)(cyclopentadienyl)(1,1,3,6,8,8-hexamethyl-1H,8H-dicyclopenta[b,h]fluorenyl)zirconium dichloride, bis(m-chlorophenyl)methylene(cyclopentadienyl)(1,1,3,6,8,8-hexamethyl-1H,8H-dicyclopenta[b,h]fluorenyl)zirconium dichloride, bis(p-tert-butylphenyl)methylene(cyclopentadienyl)(1,1,3,6,8,8-hexamethyl-1H,8H-dicyclopenta[b,h]fluorenyl)zirconium dichloride, isopropylidene(3-tert-butyl-cyclopentadienyl)(1,1,3,6,8,8-hexamethyl-1H,8H-dicyclopenta[b,h]fluorenyl)zirconium dichloride, dibutylmethylene(3-tert-butyl-cyclopentadienyl)(1,1,3,6,8,8-hexamethyl-1H,8H-dicyclopenta[b,h]fluorenyl)zirconium dichloride, cyclohexylidene(3-tert-butyl-cyclopentadienyl)(1,1,3,6,8,8-hexamethyl-1H,8H-dicyclopenta[b,h]fluorenyl)zirconium dichloride, dibenzylmethylene(3-tert-butyl-cyclopentadienyl)(1,1,3,6,8,8-hexamethyl-1H,8H-dicyclopenta[b,h]fluorenyl)zirconium dichloride, phenylmethylene(3-tert-butyl-cyclopentadienyl)(1,1,3,6,8,8-hexamethyl-1H,8H-dicyclopenta[b,h]fluorenyl)zirconium dichloride, (phenyl)(methyl)methylene(3-tert-butyl-cyclopentadienyl)(1,1,3,6,8,8-hexamethyl-1H,8H-dicyclopenta[b,h]fluorenyl)zirconium dichloride, (p-tolyl)(methyl)methylene(3-tert-butyl-cyclopentadienyl)(1,1,3,6,8,8-hexamethyl-1H,8H-dicyclopenta[b,h]fluorenyl)zirconium dichloride, (phenyl)(ethyl)methylene(3-tert-butyl-cyclopentadienyl)(1,1,3,6,8,8-hexamethyl-1H,8H-dicyclopenta[b,h]fluorenyl)zirconium dichloride, diphenylmethylene(3-tert-butyl-cyclopentadienyl)(1,1,3,6,8,8-hexamethyl-1H,8H-dicyclopenta[b,h]fluorenyl)zirconium dichloride, di-p-tolylmethylene(3-tert-butyl-cyclopentadienyl)(1,1,3,6,8,8-hexamethyl-1H,8H-dicyclopenta[b,h]fluorenyl)zirconium dichloride, bis(p-trifluoromethylphenyl)methylene(3-tert-butyl-cyclopentadienyl)(1,1,3,6,8,8-hexamethyl-1H,8H-dicyclopenta[b,h]fluorenyl)zirconium dichloride, bis(m-trifluoromethylphenyl)methylene(3-tert-butyl-cyclopentadienyl)(1,1,3,6,8,8-hexamethyl-1H,8H-dicyclopenta[b,h]fluorenyl)zirconium dichloride, bis(p-fluorophenyl)methylene(3-tert-butyl-cyclopentadienyl)(1,1,3,6,8,8-hexamethyl-1H,8H-dicyclopenta[b,h]fluorenyl)zirconium dichloride, bis(m-fluorophenyl)methylene(3-tert-butyl-cyclopentadienyl)(1,1,3,6,8,8-hexamethyl-1H,8H-dicyclopenta[b,h]fluorenyl)zirconium dichloride, bis(p-chlorophenylmethylene)(3-tert-butyl-cyclopentadienyl)(1,1,3,6,8,8-hexamethyl-1H,8H-dicyclopenta[b,h]fluorenyl)zirconium dichloride, bis(m-chlorophenyl)methylene(3-tert-butyl-cyclopentadienyl)(1,1,3,6,8,8-hexamethyl-1H,8H-dicyclopenta[b,h]fluorenyl)zirconium dichloride, bis(p-tert-butylphenyl)methylene(3-tert-butyl-cyclopentadienyl)(1,1,3,6,8,8-hexamethyl-1H,8H-dicyclopenta[b,h]fluorenyl)zirconium dichloride, isopropylidene(3-tert-butyl-5-methylcyclopentadienyl)(1,1,3,6,8,8-hexamethyl-1H,8H-dicyclopenta[b,h]fluorenyl)zirconium dichloride, dibutylmethylene(3-tert-butyl-5-methylcyclopentadienyl)(1,1,3,6,8,8-hexamethyl-1H,8H-dicyclopenta[b,h]fluorenyl)zirconium dichloride, cyclohexylidene(3-tert-butyl-5-methylcyclopentadienyl)(1,1,3,6,8,8-hexamethyl-1H,8H-dicyclopenta[b,h]fluorenyl)zirconium dichloride, dibenzylmethylene(3-tert-butyl-5-methylcyclopentadienyl)(1,1,3,6,8,8-hexamethyl-1H,8H-dicyclopenta[b,h]fluorenyl)zirconium dichloride, phenylmethylene(3-tert-butyl-5-methylcyclopentadienyl)(1,1,3,6,8,8-hexamethyl-1H,8H-dicyclopenta[b,h]fluorenyl)zirconium dichloride, (phenyl)(methyl)methylene(3-tert-butyl-5-methylcyclopentadienyl)(1,1,3,6,8,8-hexamethyl-1H,8H-dicyclopenta[b,h]fluorenyl)zirconium dichloride, (p-tolyl)(methyl)methylene(3-tert-butyl-5-methylcyclopentadienyl)(1,1,3,6,8,8-hexamethyl-1H,8H-dicyclopenta[b,h]fluorenyl)zirconium dichloride, (phenyl)(ethyl)methylene(3-tert-butyl-5-methylcyclopentadienyl)(1,1,3,6,8,8-hexamethyl-1H,8H-dicyclopenta[b,h]fluorenyl)zirconium dichloride, diphenylmethylene(3-tert-butyl-5-methylcyclopentadienyl)(1,1,3,6,8,8-hexamethyl-1H,8H-dicyclopenta[b,h]fluorenyl)zirconium dichloride, di-p-tolylmethylene(3-tert-butyl-5-methylcyclopentadienyl)(1,1,3,6,8,8-hexamethyl-1H,8H-dicyclopenta[b,h]fluorenyl)zirconium dichloride, bis(p-trifluoromethylphenyl)methylene(3-tert-butyl-5-methyl cyclopentadienyl)(1,1,3,6,8,8-hexamethyl-1H,8H-dicyclopenta[b,h]fluorenyl)zirconium dichloride, bis(m-trifluoromethylphenyl)methylene(3-tert-butyl-5-methyl cyclopentadienyl)(1,1,3,6,8,8-hexamethyl-1H,8H-dicyclopenta[b,h]fluorenyl)zirconium dichloride, bis(p-fluorophenyl)methylene(3-tert-butyl-5-methylcyclopentadienyl)(1,1,3,6,8,8-hexamethyl-1H,8H-dicyclopenta[b,h]fluorenyl)zirconium dichloride, bis(m-fluorophenyl)methylene(3-tert-butyl-5-methylcyclopentadienyl)(1,1,3,6,8,8-hexamethyl-1H,8H-dicyclopenta[b,h]fluorenyl)zirconium dichloride, bis(p-chlorophenyl)methylene(3-tert-butyl-5-methylcyclopentadienyl)(1,1,3,6,8,8-hexamethyl-1H,8H-dicyclopenta[b,h]fluorenyl)zirconium dichloride, bis(m-chlorophenyl)methylene(3-tert-butyl-5-methylcyclopentadienyl)(1,1,3,6,8,8-hexamethyl-1H,8H-dicyclopenta[b,h]fluorenyl)zirconium dichloride, bis(p-tert-butylphenyl)methylene(3-tert-butyl-5-methylcyclopentadienyl)(1,1,3,6,8,8-hexamethyl-1H,8H-dicyclopenta[b,h]fluorenyl)zirconium dichloride, isopropylidene(3-tert-butyl-5-ethylcyclopentadienyl)(1,1,3,6,8,8-hexamethyl-1H,8H-dicyclopenta[b,h]fluorenyl)zirconium dichloride, dibutylmethylene(3-tert-butyl-5-ethylcyclopentadienyl)(1,1,3,6,8,8-hexamethyl-1H,8H-dicyclopenta[b,h]fluorenyl)zirconium dichloride, cyclohexylidene(3-tert-butyl-5-ethylcyclopentadienyl)(1,1,3,6,8,8-hexamethyl-1H,8H-dicyclopenta[b,h]fluorenyl)zirconium dichloride, dibenzylmethylene(3-tert-butyl-5-ethylcyclopentadienyl)(1,1,3,6,8,8-hexamethyl-1H,8H-dicyclopenta[b,h]fluorenyl)zirconium dichloride, phenylmethylene(3-tert-butyl-5-ethylcyclopentadienyl)(1,1,3,6,8,8-hexamethyl-1H,8H-dicyclopenta[b,h]fluorenyl)zirconium dichloride, (phenyl)(methyl)methylene(3-tert-butyl-5-ethylcyclopentadienyl)(1,1,3,6,8,8-hexamethyl-1H,8H-dicyclopenta[b,h]fluorenyl)zirconium dichloride, (p-tolyl)(methyl)methylene(3-tert-butyl-5-ethylcyclopentadienyl)(1,1,3,6,8,8-hexamethyl-1H,8H-dicyclopenta[b,h]fluorenyl)zirconium dichloride, (phenyl)(ethyl)methylene(3-tert-butyl-5-ethylcyclopentadienyl)(1,1,3,6,8,8-hexamethyl-1H,8H-dicyclopenta[b,h]fluorenyl)zirconium dichloride, diphenylmethylene(3-tert-butyl-5-ethylcyclopentadienyl)(1,1,3,6,8,8-hexamethyl-1H,8H-dicyclopenta[b,h]fluorenyl)zirconium dichloride, di-p-tolylmethylene(3-tert-butyl-5-ethylcyclopentadienyl)(1,1,3,6,8,8-hexamethyl-1H,8H-dicyclopenta[b,h]fluorenyl)zirconium dichloride, bis(p-trifluoromethylphenyl)methylene(3-tert-butyl-5-ethylcyclopentadienyl)(1,1,3,6,8,8-hexamethyl-1H,8H-dicyclopenta[b,h]fluorenyl)zirconium dichloride, bis(m-trifluoromethylphenyl)methylene(3-tert-butyl-5-ethylcyclopentadienyl)(1,1,3,6,8,8-hexamethyl-1H,8H-dicyclopenta[b,h]fluorenyl)zirconium dichloride, bis(p-fluorophenyl)methylene(3-tert-butyl-5-ethylcyclopentadienyl)(1,1,3,6,8,8-hexamethyl-1H,8H-dicyclopenta[b,h]fluorenyl)zirconium dichloride, bis(m-fluorophenyl)methylene(3-tert-butyl-5-ethylcyclopentadienyl)(1,1,3,6,8,8-hexamethyl-1H,8H-dicyclopenta[b,h]fluorenyl)zirconium dichloride, bis(p-chlorophenylmethylene)(3-tert-butyl-5-ethylcyclopentadienyl)(1,1,3,6,8,8-hexamethyl-1H,8H-dicyclopenta[b,h]fluorenyl)zirconium dichloride, bis(m-chlorophenyl)methylene(3-tert-butyl-5-ethylcyclopentadienyl)(1,1,3,6,8,8-hexamethyl-1H,8H- dicyclopenta[b,h]fluorenyl)zirconium dichloride, bis(p-tert-butylphenyl)methylene(3-tert-butyl-5-ethylcyclopentadienyl)(1,1,3,6,8,8-hexamethyl-1H,8H-dicyclopenta[b,h]fluorenyl)zirconium dichloride, isopropylidene(3,5-dimethylcyclopentadienyl)(1,1,3,6,8,8-hexamethyl-1H,8H-dicyclopenta[b,h]fluorenyl)zirconium dichloride, dibutylmethylene(3,5-dimethylcyclopentadienyl)(1,1,3,6,8,8-hexamethyl-1H,8H-dicyclopenta[b,h]fluorenyl)zirconium dichloride, cyclohexylidene(3,5-dimethylcyclopentadienyl)(1,1,3,6,8,8-hexamethyl-1H,8H-dicyclopenta[b,h]fluorenyl)zirconium dichloride, dibenzylmethylene(3,5-dimethylcyclopentadienyl)(1,1,3,6,8,8-hexamethyl-1H,8H-dicyclopenta[b,h]fluorenyl)zirconium dichloride, phenylmethylene(3,5-dimethylcyclopentadienyl)(1,1,3,6,8,8-hexamethyl-1H,8H-dicyclopenta[b,h]fluorenyl)zirconium dichloride, (phenyl)(methyl)methylene(3,5-dimethylcyclopentadienyl)(1,1,3,6,8,8-hexamethyl-1H,8H-dicyclopenta[b,h]fluorenyl)zirconium dichloride, (p-tolyl)(methyl)methylene(3,5-dimethylcyclopentadienyl)(1,1,3,6,8,8-hexamethyl-1H,8H-dicyclopenta[b,h]fluorenyl)zirconium dichloride, (phenyl)(ethyl)methylene(3,5-dimethylcyclopentadienyl)(1,1,3,6,8,8-hexamethyl-1H,8H-dicyclopenta[b,h]fluorenyl)zirconium dichloride, diphenylmethylene(3,5-dimethylcyclopentadienyl)(1,1,3,6,8,8-hexamethyl-1H,8H-dicyclopenta[b,h]fluorenyl)zirconium dichloride, di-p-tolylmethylene(3,5-dimethylcyclopentadienyl)(1,1,3,6,8,8-hexamethyl-1H,8H-dicyclopenta[b,h]fluorenyl)zirconium dichloride, bis(p-trifluoromethylphenyl)methylene(3,5-dimethylcyclopentadienyl)(1,1,3,6,8,8-hexamethyl-1H,8H-dicyclopenta[b,h]fluorenyl)zirconium dichloride, bis(m-trifluoromethylphenyl)methylene(3,5-dimethylcyclopentadienyl)(1,1,3,6,8,8-hexamethyl-1H,8H-dicyclopenta[b,h]fluorenyl)zirconium dichloride, bis(p-fluorophenyl)methylene(3,5-dimethylcyclopentadienyl)(1,1,3,6,8,8-hexamethyl-1H,8H-dicyclopenta[b,h]fluorenyl)zirconium dichloride, bis(m-fluorophenyl)methylene(3,5-dimethylcyclopentadienyl)(1,1,3,6,8,8-hexamethyl-1H,8H-dicyclopenta[b,h]fluorenyl)zirconium dichloride, bis(p-chlorophenylmethylene)(3,5-dimethylcyclopentadienyl)(1,1,3,6,8,8-hexamethyl-1H,8H-dicyclopenta[b,h]fluorenyl)zirconium dichloride, bis(m-chlorophenyl)methylene(3,5-dimethylcyclopentadienyl)(1,1,3,6,8,8-hexamethyl-1H,8H-dicyclopenta[b,h]fluorenyl)zirconium dichloride, bis(p-tert-butylphenyl)methylene(3,5-dimethylcyclopentadienyl)(1,1,3,6,8,8-hexamethyl-1H,8H-dicyclopenta[b,h]fluorenyl)zirconium dichloride, isopropylidene(cyclopentadienyl)(1,1,8,8-tetramethyl-1H,8H-dicyclopenta[b,h]fluorenyl)zirconium dichloride, dibutylmethylene(cyclopentadienyl)(1,1,8,8-tetramethyl-1H,8H-dicyclopenta[b,h]fluorenyl)zirconium dichloride, cyclohexylidene(cyclopentadienyl)(1,1,8,8-tetramethyl-1H,8H-dicyclopenta[b,h]fluorenyl)zirconium dichloride, dibenzylmethylene(cyclopentadienyl)(1,1,8,8-tetramethyl-1H,8H-dicyclopenta[b,h]fluorenyl)zirconium dichloride, phenylmethylene(cyclopentadienyl)(1,1,8,8-tetramethyl-1H,8H-dicyclopenta[b,h]fluorenyl)zirconium dichloride, (phenyl)(methyl)methylene(cyclopentadienyl)(1,1,8,8-tetramethyl-1H,8H-dicyclopenta[b,h]fluorenyl)zirconium dichloride, (p-tolyl)(methyl)methylene(cyclopentadienyl)(1,1,8,8-tetramethyl-1H,8H-dicyclopenta[b,h]fluorenyl)zirconium dichloride, (phenyl)(ethyl)methylene(cyclopentadienyl)(1,1,8,8-tetramethyl-1H,8H-dicyclopenta[b,h]fluorenyl)zirconium dichloride, diphenylmethylene(cyclopentadienyl)(1,1,8,8-tetramethyl-1H,8H-dicyclopenta[b,h]fluorenyl)zirconium dichloride, di-p-tolylmethylene(cyclopentadienyl)(1,1,8,8-tetramethyl-1H,8H-dicyclopenta[b,h]fluorenyl)zirconium dichloride, bis(p-trifluoromethylphenyl)methylene(cyclopentadienyl)(1,1,8,8-tetramethyl-1H,8H-dicyclopenta[b,h]fluorenyl)zirconium dichloride, bis(m-trifluoromethylphenyl)methylene(cyclopentadienyl)(1,1,8,8-tetramethyl-1H,8H-dicyclopenta[b,h]fluorenyl)zirconium dichloride, bis(p-fluorophenyl)methylene(cyclopentadienyl)(1,1,8,8-tetramethyl-1H,8H-dicyclopenta[b,h]fluorenyl)zirconium dichloride, bis(m-fluorophenyl)methylene(cyclopentadienyl)(1,1,8,8-tetramethyl-1H,8H-dicyclopenta[b,h]fluorenyl)zirconium dichloride, bis(p-chlorophenyl)methylene(cyclopentadienyl)(1,1,8,8-tetramethyl-1H,8H-dicyclopenta[b,h]fluorenyl)zirconium dichloride, bis(m-chlorophenyl)methylene(cyclopentadienyl)(1,1,8,8-tetramethyl-1H,8H-dicyclopenta[b,h]fluorenyl)zirconium dichloride, bis(p-tert-butylphenyl)methylene(cyclopentadienyl)(1,1,8,8-tetramethyl-1H,8H-dicyclopenta[b,h]fluorenyl)zirconium dichloride, isopropylidene(3-tert-butyl-cyclopentadienyl)(1,1,8,8-tetramethyl-1H,8H-dicyclopenta[b,h]fluorenyl)zirconium dichloride, dibutylmethylene(3-tert-butyl-cyclopentadienyl)(1,1,8,8-tetramethyl-1H,8H-dicyclopenta[b,h]fluorenyl)zirconium dichloride, cyclohexylidene(3-tert-butyl-cyclopentadienyl)(1,1,8,8-tetramethyl-1H,8H-dicyclopenta[b,h]fluorenyl)zirconium dichloride, dibenzylmethylene(3-tert-butyl-cyclopentadienyl)(1,1,8,8-tetramethyl-1H,8H-dicyclopenta[b,h]fluorenyl)zirconium dichloride, phenylmethylene(3-tert-butyl-cyclopentadienyl)(1,1,8,8-tetramethyl-1H,8H-dicyclopenta[b,h]fluorenyl)zirconium dichloride, (phenyl)(methyl)methylene(3-tert-butyl-cyclopentadienyl)(1,1,8,8-tetramethyl-1H,8H-dicyclopenta[b,h]fluorenyl)zirconium dichloride, (p-tolyl)(methyl)methylene(3-tert-butyl-cyclopentadienyl)(1,1,8,8-tetramethyl-1H,8H-dicyclopenta[b,h]fluorenyl)zirconium dichloride, (phenyl)(ethyl)methylene(3-tert-butyl-cyclopentadienyl)(1,1,8,8-tetramethyl-1H,8H-dicyclopenta[b,h]fluorenyl)zirconium dichloride, diphenylmethylene(3-tert-butyl-cyclopentadienyl)(1,1,8,8-tetramethyl-1H,8H-dicyclopenta[b,h]fluorenyl)zirconium dichloride, di-p-tolylmethylene(3-tert-butyl-cyclopentadienyl)(1,1,8,8-tetramethyl-1H,8H-dicyclopenta[b,h]fluorenyl)zirconium dichloride, bis(p-trifluoromethylphenyl)methylene(3-tert-butyl-cyclopentadienyl)(1,1,8,8-tetramethyl-1H,8H-dicyclopenta[b,h]fluorenyl)zirconium dichloride, bis(m-trifluoromethylphenyl)methylene(3-tert-butyl-cyclopentadienyl)(1,1,8,8-tetramethyl-1H,8H-dicyclopenta[b,h]fluorenyl)zirconium dichloride, bis(p-fluorophenyl)methylene(3-tert-butyl-cyclopentadienyl)(1,1,8,8-tetramethyl-1H,8H-dicyclopenta[b,h]fluorenyl)zirconium dichloride, bis(m-fluorophenyl)methylene(3-tert-butyl-cyclopentadienyl)(1,1,8,8-tetramethyl-1H,, 8H-dicyclopenta[b,h]fluorenyl)zirconium dichloride, bis(p-chlorophenylmethylene)(3-tert-butyl-cyclopentadienyl)(1,1,8,8-tetramethyl-1H,8H-dicyclopenta[b,h]fluorenyl)zirconium dichloride, bis(m-chlorophenyl)methylene(3-tert-butyl-cyclopentadienyl)(1,1,8,8-tetramethyl-1H,8H-dicyclopenta[b,h]fluorenyl)zirconium dichloride, bis(p-tert-butylphenyl)methylene(3-tert-butyl-cyclopentadienyl)(1,1,8,8-tetramethyl-1H,8H-dicyclopenta[b,h]fluorenyl)zirconium dichloride, isopropylidene(3-tert-butyl-5-methylcyclopentadienyl)(1,1,8,8-tetramethyl-1H,8H-dicyclopenta[b,h]fluorenyl)zirconium dichloride, dibutylmethylene(3-tert-butyl-5-methylcyclopentadienyl)(1,1,8,8-tetramethyl-1H,8H-dicyclopenta[b,h]fluorenyl)zirconium dichloride, cyclohexylidene(3-tert-butyl-5-methylcyclopentadienyl)(1,1,8,8-tetramethyl-1H,8H-dicyclopenta[b,h]fluorenyl)zirconium dichloride, dibenzylmethylene(3-tert-butyl-5-methylcyclopentadienyl)(1,1,8,8-tetramethyl-1H,8H-dicyclopenta[b,h]fluorenyl)zirconium dichloride, phenylmethylene(3- tert-butyl-5-methylcyclopentadienyl)(1,1,8,8-tetramethyl-1H,8H-dicyclopenta[b,h]fluorenyl)zirconium dichloride, (phenyl)(methyl)methylene(3-tert-butyl-5-methylcyclopentadienyl)(1,1,8,8-tetramethyl-1H,8H-dicyclopenta[b,h]fluorenyl)zirconium dichloride, (p-tolyl)(methyl)methylene(3-tert-butyl-5-methylcyclopentadienyl)(1,1,8,8-tetramethyl-1H,8H-dicyclopenta[b,h]fluorenyl)zirconium dichloride, (phenyl)(ethyl)methylene(3-tert-butyl-5-methylcyclopentadienyl)(1,1,8,8-tetramethyl-1H,8H-dicyclopenta[b,h]fluorenyl)zirconium dichloride, diphenylmethylene(3-tert-butyl-5-methylcyclopentadienyl)(1,1,8,8-tetramethyl-1H,8H-dicyclopenta[b,h]fluorenyl)zirconium dichloride, di-p-tolylmethylene(3-tert-butyl-5-methylcyclopentadienyl)(1,1,8,8-tetramethyl-1H,8H-dicyclopenta[b,h]fluorenyl)zirconium dichloride, bis(p-trifluoromethylphenyl)methylene(3-tert-butyl-5-methyl cyclopentadienyl)(1,1,8,8-tetramethyl-1H,8H-dicyclopenta[b,h]fluorenyl)zirconium dichloride, bis(m-trifluoromethylphenyl)methylene(3-tert-butyl-5-methyl cyclopentadienyl)(1,1,8,8-tetramethyl-1H,8H-dicyclopenta[b,h]fluorenyl)zirconium dichloride, bis(p-fluorophenyl)methylene(3-tert-butyl-5-methylcyclopentadienyl)(1,1,8,8-tetramethyl-1H,8H-dicyclopenta[b,h]fluorenyl)zirconium dichloride, bis(m-fluorophenyl)methylene(3-tert-butyl-5-methylcyclopentadienyl)(1,1,8,8-tetramethyl-1H,8H-dicyclopenta[b,h]fluorenyl)zirconium dichloride, bis(p-chlorophenylmethylene)(3-tert-butyl-5-methylcyclopentadienyl)(1,1,8,8-tetramethyl-1H,8H-dicyclopenta[b,h]fluorenyl)zirconium dichloride, bis(m-chlorophenyl)methylene(3-tert-butyl-5-methylcyclopentadienyl)(1,1,8,8-tetramethyl-1H,8H-dicyclopenta[b,h]fluorenyl)zirconium dichloride, bis(p-tert-butylphenyl)methylene(3-tert-butyl-5-methylcyclopentadienyl)(1,1,8,8-tetramethyl-1H,8H-dicyclopenta[b,h]fluorenyl)zirconium dichloride, isopropylidene(3-tert-butyl-5-ethylcyclopentadienyl)(1,1,8,8-tetramethyl-1H,8H-dicyclopenta[b,h]fluorenyl)zirconium dichloride, dibutylmethylene(3-tert-butyl-5-ethylcyclopentadienyl)(1,1,8,8-tetramethyl-1H,8H-dicyclopenta[b,h]fluorenyl)zirconium dichloride, cyclohexylidene(3-tert-butyl-5-ethylcyclopentadienyl)(1,1,8,8-tetramethyl-1H,8H-dicyclopenta[b,h]fluorenyl)zirconium dichloride, dibenzylmethylene(3-tert-butyl-5-ethylcyclopentadienyl)(1,1,8,8-tetramethyl-1H,8H-dicyclopenta[b,h]fluorenyl)zirconium dichloride, phenylmethylene(3-tert-butyl-5-ethylcyclopentadienyl)(1,1,8,8-tetramethyl-1H,8H-dicyclopenta[b,h]fluorenyl)zirconium dichloride, (phenyl)(methyl)methylene(3-tert-butyl-5-ethylcyclopentadienyl)(1,1,8,8-tetramethyl-1H,8H-dicyclopenta[b,h]fluorenyl)zirconium dichloride, (p-tolyl)(methyl)methylene(3-tert-butyl-5-ethylcyclopentadienyl)(1,1,8,8-tetramethyl-1H,8H-dicyclopenta[b,h]fluorenyl)zirconium dichloride, (phenyl)(ethyl)methylene(3-tert-butyl-5-ethylcyclopentadienyl)(1,1,8,8-tetramethyl-1H,8H-dicyclopenta[b,h]fluorenyl)zirconium dichloride, diphenylmethylene(3-tert-butyl-5-ethylcyclopentadienyl)(1,1,8,8-tetramethyl-1H,8H-dicyclopenta[b,h]fluorenyl)zirconium dichloride, di-p-tolylmethylene(3-tert-butyl-5-ethylcyclopentadienyl)(1,1,8,8-tetramethyl-1H,8H-dicyclopenta[b,h]fluorenyl)zirconium dichloride, bis(p-trifluoromethylphenyl)methylene(3-tert-butyl-5-ethylcyclopentadienyl)(1,1,8,8-tetramethyl-1H,8H-dicyclopenta[b,h]fluorenyl)zirconium dichloride, bis(m-trifluoromethylphenyl)methylene(3-tert-butyl-5-ethylcyclopentadienyl)(1,1,8,8-tetramethyl-1H,8H-dicyclopenta[b,h]fluorenyl)zirconium dichloride, bis(p-fluorophenyl)methylene(3-tert-butyl-5-ethylcyclopentadienyl)(1,1,8,8-tetramethyl-1H,8H-dicyclopenta[b,h]fluorenyl)zirconium dichloride, bis(m-fluorophenyl)methylene(3-tert-butyl-5-ethylcyclopentadienyl)(1,1,8,8-tetramethyl-1H,8H-dicyclopenta[b,h]fluorenyl)zirconium dichloride, bis(p-chlorophenylmethylene)(3-tert-butyl-5-ethylcyclopentadienyl)(1,1,8,8-tetramethyl-1H,8H-dicyclopenta[b,h]fluorenyl)zirconium dichloride, bis(m-chlorophenyl)methylene(3-tert-butyl-5-ethylcyclopentadienyl)(1,1,8,8-tetramethyl-1H,8H-dicyclopenta[b,h]fluorenyl)zirconium dichloride, bis(p-tert-butylphenyl)methylene(3-tert-butyl-5-ethylcyclopentadienyl)(1,1,8,8-tetramethyl-1H,8H-dicyclopenta[b,h]fluorenyl)zirconium dichloride, isopropylidene(3,5-dimethylcyclopentadienyl)(1,1,8,8-tetramethyl-1H,8H-dicyclopenta[b,h]fluorenyl)zirconium dichloride, dibutylmethylene(3,5-dimethylcyclopentadienyl)(1,1,8,8-tetramethyl-1H,8H-dicyclopenta[b,h]fluorenyl)zirconium dichloride, cyclohexylidene(3,5-dimethylcyclopentadienyl)(1,1,8,8-tetramethyl-1H,8H-dicyclopenta[b,h]fluorenyl)zirconium dichloride, dibenzylmethylene(3,5-dimethylcyclopentadienyl)(1,1,8,8-tetramethyl-1H,8H-dicyclopenta[b,h]fluorenyl)zirconium dichloride, phenylmethylene(3,5-dimethylcyclopentadienyl)(1,1,8,8-tetramethyl-1H,8H-dicyclopenta[b,h]fluorenyl)zirconium dichloride, (phenyl)(methyl)methylene(3,5-dimethylcyclopentadienyl)(1,1,8,8-tetramethyl-1H,8H-dicyclopenta[b,h]fluorenyl)zirconium dichloride, (p-tolyl)(methyl)methylene(3,5-dimethylcyclopentadienyl)(1,1,8,8-tetramethyl-1H,8H-dicyclopenta[b,h]fluorenyl)zirconium dichloride, (phenyl)(ethyl)methylene(3,5-dimethylcyclopentadienyl)(1,1,8,8-tetramethyl-1H,8H-dicyclopenta[b,h]fluorenyl)zirconium dichloride, diphenylmethylene(3,5-dimethylcyclopentadienyl)(1,1,8,8-tetramethyl-1H,8H-dicyclopenta[b,h]fluorenyl)zirconium dichloride, di-p-tolylmethylene(3,5-dimethylcyclopentadienyl)(1,1,8,8-tetramethyl-1H,8H-dicyclopenta[b,h]fluorenyl)zirconium dichloride, bis(p-trifluoromethylphenyl)methylene(3,5-dimethylcyclopentadienyl)(1,1,8,8-tetramethyl-1H,8H-dicyclopenta[b,h]fluorenyl)zirconium dichloride, bis(m-trifluoromethylphenyl)methylene(3,5-dimethylcyclopentadienyl)(1,1,8,8-tetramethyl-1H,8H-dicyclopenta[b,h]fluorenyl)zirconium dichloride, bis(p-fluorophenyl)methylene(3,5-dimethylcyclopentadienyl)(1,1,8,8-tetramethyl-1H,8H-dicyclopenta[b,h]fluorenyl)zirconium dichloride, bis(m-fluorophenyl)methylene(3,5-dimethylcyclopentadienyl)(1,1,8,8-tetramethyl-1H,8H-dicyclopenta[b,h]fluorenyl)zirconium dichloride, bis(p-chlorophenylmethylene)(3,5-dimethylcyclopentadienyl)(1,1,8,8-tetramethyl-1H,8H-dicyclopenta[b,h]fluorenyl)zirconium dichloride, bis(m-chlorophenyl)methylene(3,5-dimethylcyclopentadienyl)(1,1,8,8-tetramethyl-1H,8H-dicyclopenta[b,h]fluorenyl)zirconium dichloride, bis(p-tert-butylphenyl)methylene(3,5-dimethylcyclopentadienyl)(1,1,8,8-tetramethyl-1H,8H-dicyclopenta[b,h]fluorenyl)zirconium dichloride, isopropylidene(cyclopentadienyl)(3,6-di-tert-butyl-1,1,8,8-tetramethyl-1H,8H-dicyclopenta[b,h]fluorenyl)zirconium dichloride, dibutylmethylene(cyclopentadienyl)(3,6-di-tert-butyl-1,1,8,8-tetramethyl-1H,8H-dicyclopenta[b,h]fluorenyl)zirconium dichloride, cyclohexylidene(cyclopentadienyl)(3,6-di-tert-butyl-1,1,8,8-tetramethyl-1H,8H-dicyclopenta[b,h]fluorenyl)zirconium dichloride, dibenzylmethylene(cyclopentadienyl)(3,6-di-tert-butyl-1,1,8,8-tetramethyl-1H,8H-dicyclopenta[b,h]fluorenyl)zirconium dichloride, phenylmethylene(cyclopentadienyl)(3,6-di-tert-butyl-1,1,8,8-tetramethyl-1H,8H-dicyclopenta[b,h]fluorenyl)zirconium dichloride, (phenyl)(methyl)methylene(cyclopentadienyl)(3,6-di-tert-butyl-1,1, 8,8-tetramethyl-1H,8H-dicyclopenta[b,h]fluorenyl)zirconium dichloride, (p-tolyl)(methyl)methylene(cyclopentadienyl)(3,6-di-tert-butyl-1,1,8,8-tetramethyl-1H,8H-dicyclopenta[b,h]fluorenyl)zirconium dichloride, (phenyl)(ethyl)methylene(cyclopentadienyl)(3,6-di-tert-butyl-1,1,8,8-tetramethyl-1H,8H-dicyclopenta[b,h]fluorenyl)zirconium dichloride, diphenylmethylene(cyclopentadienyl)(3,6-di-tert-butyl-1,1,8,8-tetramethyl-1H,8H-dicyclopenta[b,h]fluorenyl)zirconium dichloride, di-p-tolylmethylene(cyclopentadienyl)(3,6-di-tert-butyl-1,1,8,8-tetramethyl-1H,8H-dicyclopenta[b,h]fluorenyl)zirconium dichloride, bis(p-trifluoromethylphenyl)methylene(cyclopentadienyl)(3,6-di-tert-butyl-1,1,8,8-tetramethyl-1H,8H-dicyclopenta[b,h]fluorenyl)zirconium dichloride, bis(m-trifluoromethylphenyl)methylene(cyclopentadienyl)(3,6-di-tert-butyl-1,1,8,8-tetramethyl-1H,8H-dicyclopenta[b,h]fluorenyl)zirconium dichloride, bis(p-fluorophenyl)methylene(cyclopentadienyl)(3,6-di-tert-butyl-1,1,8,8-tetramethyl-1H,8H-dicyclopenta[b,h]fluorenyl)zirconium dichloride, bis(m-fluorophenyl)methylene(cyclopentadienyl)(3,6-di-tert-butyl-1,1,8,8-tetramethyl-1H,8H-dicyclopenta[b,h]fluorenyl)zirconium dichloride, bis(p-chlorophenylmethylene)(cyclopentadienyl)(3,6-di-tert-butyl-1,1,8,8-tetramethyl-1H,8H-dicyclopenta[b,h]fluorenyl)zirconium dichloride, bis(m-chlorophenyl)methylene(cyclopentadienyl)(3,6-di-tert-butyl-1,1,8,8-tetramethyl-1H,8H-dicyclopenta[b,h]fluorenyl)zirconium dichloride, bis(p-tert-butylphenyl)methylene(cyclopentadienyl)(3,6-di-tert-butyl-1,1,8,8-tetramethyl-1H,8H-dicyclopenta[b,h]fluorenyl)zirconium dichloride, isopropylidene(3-tert-butyl-cyclopentadienyl)(3,6-di-tert-butyl-1,1,8,8-tetramethyl-1H,8H-dicyclopenta[b,h]fluorenyl)zirconium dichloride, dibutylmethylene(3-tert-butyl-cyclopentadienyl)(3,6-di-tert-butyl-1,1,8,8-tetramethyl-1H,8H-dicyclopenta[b,h]fluorenyl)zirconium dichloride, cyclohexylidene(3-tert-butyl-cyclopentadienyl)(3,6-di-tert-butyl-1,1,8,8-tetramethyl-1H,8H-dicyclopenta[b,h]fluorenyl)zirconium dichloride, dibenzylmethylene(3-tert-butyl-cyclopentadienyl)(3,6-di-ter t-butyl-1,1,8,8-tetramethyl-1H,8H-dicyclopenta[b,h]fluorenyl)zirconium dichloride, phenylmethylene(3-tert-butyl-cyclopentadienyl)(3,6-di-tert-butyl-1,1,8,8-tetramethyl-1H,8H-dicyclopenta[b,h]fluorenyl)zirconium dichloride, (phenyl)(methyl)methylene(3-tert-butyl-cyclopentadienyl)(3,6-di-tert-butyl-1,1,8,8-tetramethyl-1H,8H-dicyclopenta[b,h]fluorenyl)zirconium dichloride, (p-tolyl)(methyl)methylene(3-tert-butyl-cyclopentadienyl)(3,6-di-tert-butyl-1,1,8,8-tetramethyl-1H,8H-dicyclopenta[b,h]fluorenyl)zirconium dichloride, (phenyl)(ethyl)methylene(3-tert-butyl-cyclopentadienyl)(3,6-di-tert-butyl-1,1,8,8-tetramethyl-1H,8H-dicyclopenta[b,h]fluorenyl)zirconium dichloride, diphenylmethylene(3-tert-butyl-cyclopentadienyl)(3,6-di-ter t-butyl-1,1,8,8-tetramethyl-1H,8H-dicyclopenta[b,h]fluorenyl)zirconium dichloride, di-p-tolylmethylene(3-tert-butyl-cyclopentadienyl)(3,6-di-tert-butyl-1,1,8,8-tetramethyl-1H,8H-dicyclopenta[b,h]fluorenyl)zirconium dichloride, bis(p-trifluoromethylphenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(m-trifluoromethylphenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(p-fluorophenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(m-fluorophenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(p-chlorophenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(m-chlorophenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, bis(p-tert-butylphenyl)methylene(3-tert-butyl-cyclopentadienyl)(3,6-di-tert-butyl-1,1,8,8-tetramethyl-1H,8H-dicyclopenta[b,h]fluorenyl)zirconium dichloride, isopropylidene(3-tert-butyl-5-methylcyclopentadienyl)(3,6-di-tert-butyl-1,1,8,8-tetramethyl-1H,8H-dicyclopenta[b,h]fluorenyl)zirconium dichloride, dibutylmethylene(3-tert-butyl-5-methylcyclopentadienyl)(3,6-di-tert-butyl-1,1,8,8-tetramethyl-1H,8H-dicyclopenta[b,h]fluorenyl)zirconium dichloride, cyclohexylidene(3-tert-butyl-5-methylcyclopentadienyl)(3,6-di-tert-butyl-1,1,8,8-tetramethyl-1H,8H-dicyclopenta[b,h]fluorenyl)zirconium dichloride, dibenzylmethylene(3-tert-butyl-5-methylcyclopentadienyl)(3,6-di-tert-butyl-1,1,8,8-tetramethyl-1H,8H-dicyclopenta[b,h]fluorenyl)zirconium dichloride, phenylmethylene(3-tert-butyl-5-methylcyclopentadienyl)(3,6-di-tert-butyl-1,1,8,8-tetramethyl-1H,8H-dicyclopenta[b,h]fluorenyl)zirconium dichloride, (phenyl)(methyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, (p-tolyl)(methyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, (phenyl)(ethyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, diphenylmethylene(3-tert-butyl-5-methylcyclopentadienyl)(3,6-di-tert-butyl-1,1,8,8-tetramethyl-1H,8H-dicyclopenta[b,h]fluorenyl)zirconium dichloride, di-p-tolylmethylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(p-trifluoromethylphenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(m-trifluoromethylphenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(p-fluorophenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(m-fluorophenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(p-chlorophenylmethylene)(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(m-chlorophenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, bis(p-tert-butylphenyl)methylene(3-tert-butyl-5-methylcyclopentadienyl)(3,6-di-tert-butyl-1,1,8,8-tetramethyl-1H,8H-dicyclopenta[b,h]fluorenyl)zirconium dichloride, isopropylidene(3-tert-butyl-5-ethylcyclopentadienyl)(3,6-di-tert-butyl-1,1,8,8-tetramethyl-1H,8H-dicyclopenta[b,h]fluorenyl)zirconium dichloride, dibutylmethylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, cyclohexylidene(3-tert-butyl-5-ethylcyclopentadienyl)(3,6-di-tert-butyl-1,1,8,8-tetramethyl-1H,8H-dicyclopenta[b,h]fluorenyl)zirconium dichloride, dibenzylmethylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, phenylmethylene(3-tertbutyl-5-ethylcyclopentadienyl)(3,6-di-tert-butyl-1,1,8,8-tetramethyl-1H,8H-dicyclopenta[b,h]fluorenyl)zirconium dichloride, (phenyl)(methyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, (p-tolyl)(methyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, (phenyl)(ethyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, diphenylmethylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, di-p-tolylmethylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(p-trifluoromethylphenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(m-trifluoromethylphenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(p-fluorophenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(m-fluorophenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(p-chlorophenylmethylene)(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(m-chlorophenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, bis(p-tert-butylphenyl)methylene(3-tert-butyl-5-ethylcyclopentadienyl)(3,6-di-tert-butyl-1,1,8,8-tetramethyl-1H,8H-dicyclopenta[b,h]fluorenyl)zirconium dichloride, isopropylidene(3,5-dimethylcyclopentadienyl)(3,6-di-tert-butyl-1,1,8,8-tetramethyl-1H,8H-dicyclopenta[b,h]fluorenyl)zirconium dichloride, dibutylmethylene(3,5-dimethylcyclopentadienyl)(3,6-di-tert-butyl-1,1,8,8-tetramethyl-1H,8H-dicyclopenta[b,h]fluorenyl)zirconium dichloride, cyclohexylidene(3,5-dimethylcyclopentadienyl)(3,6-di-tert-butyl-1,1,8,8-tetramethyl-1H,8H-dicyclopenta[b,h]fluorenyl)zirconium dichloride, dibenzylmethylene(3,5-dimethylcyclopentadienyl)(3,6-di-tert-butyl-1,1,8,8-tetramethyl-1H,8H-dicyclopenta[b,h]fluorenyl)zirconium dichloride, phenylmethylene(3,5-dimethylcyclopentadienyl)(3,6-di-tert-butyl-1,1,8,8-tetramethyl-1H,8H-dicyclopenta[b,h]fluorenyl)zirconium dichloride, (phenyl)(methyl)methylene(3,5-dimethylcyclopentadienyl)(3,6-di-tert-butyl-1,1,8,8-tetramethyl-1H,8H-dicyclopenta[b,h]fluorenyl)zirconium dichloride, (p-tolyl)(methyl)methylene(3,5-dimethylcyclopentadienyl)(3,6-di-tert-butyl-1,1,8,8-tetramethyl-1H,8H-dicyclopenta[b,h]fluorenyl)zirconium dichloride, (phenyl)(ethyl)methylene(3,5-dimethylcyclopentadienyl)(3,6-di-tert-butyl-1,1,8,8-tetramethyl-1H,8H-dicyclopenta[b,h]fluorenyl)zirconium dichloride, diphenylmethylene(3,5-dimethylcyclopentadienyl)(3,6-di-tert-butyl-1,1,8,8-tetramethyl-1H,8H-dicyclopenta[b,h]fluorenyl)zirconium dichloride, di-p-tolylmethylene(3,5-dimethylcyclopentadienyl)(3,6-di-tert-butyl-1,1,8,8-tetramethyl-1H,8H-dicyclopenta[b,h]fluorenyl)zirconium dichloride, bis(p-trifluoromethylphenyl)methylene(3,5-dimethylcyclopentadienyl)(3,6-di-tert-butyl-1,1,8,8-tetramethyl-1H,8H-dicyclopenta[b,h]fluorenyl)zirconium dichloride, bis(m-trifluoromethylphenyl)methylene(3,5-dimethylcyclopentadienyl)(3,6-di-tert-butyl-1,1,8,8-tetramethyl-1H,8H-dicyclopenta[b,h]fluorenyl)zirconium dichloride, bis(p-fluorophenyl)methylene(3,5-dimethylcyclopentadienyl)(3,6-di-tert-butyl-1,1,8,8-tetramethyl-1H,8H-dicyclopenta[b,h]fluorenyl)zirconium dichloride, bis(m-fluorophenyl)methylene(3,5-dimethylcyclopentadienyl)(3,6-di-tert-butyl-1,1,8,8-tetramethyl-1H,8H-dicyclopenta[b,h]fluorenyl)zirconium dichloride, bis(p-chlorophenylmethylene)(3,5-dimethylcyclopentadienyl)(3,6-di-tert-butyl-1,1,8,8-tetramethyl-1H,8H-dicyclopenta[b,h]fluorenyl)zirconium dichloride, bis(m-chlorophenyl)methylene(3,5-dimethylcyclopentadienyl)(3,6-di-tert-butyl-1,1,8,8-tetramethyl-1H,8H-dicyclopenta[b,h]fluorenyl)zirconium dichloride, bis(p-tert-butylphenyl)methylene(3,5-dimethylcyclopentadienyl)(3,6-di-tert-butyl-1,1,8,8-tetramethyl-1H,8H-dicyclopenta[b,h]fluorenyl)zirconium dichloride, isopropylidene(cyclopentadienyl)(3,6-divinylfluorenyl)zirconium dichloride, dibutylmethylene(cyclopentadienyl)(3,6-divinylfluorenyl)zirconium dichloride, cyclohexylidene(cyclopentadienyl)(3,6-divinylfluorenyl)zirconium dichloride, dibenzylmethylene(cyclopentadienyl)(3,6-divinylfluorenyl)zirconium dichloride, phenylmethylene(cyclopentadienyl)(3,6-divinylfluorenyl)zirconium dichloride, (phenyl)(methyl)methylene(cyclopentadienyl)(3,6-divinylfluorenyl)zirconium dichloride, (p-tolyl)(methyl)methylene(cyclopentadienyl)(3,6-divinylfluorenyl)zirconium dichloride, (phenyl)(ethyl)methylene(cyclopentadienyl)(3,6-divinylfluorenyl)zirconium dichloride, diphenylmethylene(cyclopentadienyl)(3,6-divinylfluorenyl)zirconium dichloride, di-p-tolylmethylene(cyclopentadienyl)(3,6-divinylfluorenyl)zirconium dichloride, bis(p-trifluoromethylphenyl)methylene(cyclopentadienyl)(3,6-divinylfluorenyl)zirconium dichloride, bis(m-trifluoromethylphenyl)methylene(cyclopentadienyl)(3,6-divinylfluorenyl)zirconium dichloride, bis(p-fluorophenyl)methylene(cyclopentadienyl)(3,6-divinylfluorenyl)zirconium dichloride, bis(m-fluorophenyl)methylene(cyclopentadienyl)(3,6-divinylfluorenyl)zirconium dichloride, bis(p-chlorophenylmethylene)(cyclopentadienyl)(3,6-divinylfluorenyl)zirconium dichloride, bis(m-chlorophenyl)methylene(cyclopentadienyl)(3,6-divinylfluorenyl)zirconium dichloride, bis(p-tert-butylphenyl)methylene(cyclopentadienyl)(3,6-divinylfluorenyl)zirconium dichloride, isopropylidene(3-tert-butyl-cyclopentadienyl)(3,6-divinylfluorenyl)zirconium dichloride, dibutylmethylene(3-tert-butyl-cyclopentadienyl)(3,6-divinyl fluorenyl)zirconium dichloride, cyclohexylidene(3-tert-butyl-cyclopentadienyl)(3,6-divinylfluorenyl)zirconium dichloride, dibenzylmethylene(3-tert-butyl-cyclopentadienyl)(3,6-divinylfluorenyl)zirconium dichloride, phenylmethylene(3-tert-butyl-cyclopentadienyl)(3,6-divinylfluorenyl)zirconium dichloride, (phenyl)(methyl)methylene(3-tert-butyl-cyclopentadienyl)(3,6-divinylfluorenyl)zirconium dichloride, (p-tolyl)(methyl)methylene(3-tert-butyl-cyclopentadienyl)(3,6-divinylfluorenyl)zirconium dichloride, (phenyl)(ethyl)methylene(3-tert-butyl-cyclopentadienyl)(3,6-divinylfluorenyl)zirconium dichloride, diphenylmethylene(3-tert-butyl-cyclopentadienyl)(3,6-divinylfluorenyl)zirconium dichloride, di-p-tolylmethylene(3-tert-butyl-cyclopentadienyl)(3,6-divinylfluorenyl)zirconium dichloride, bis(p-trifluoromethylphenyl)methylene(3-tert-butyl-cyclopentadienyl)(3,6-divinylfluorenyl)zirconium dichloride, bis(m-trifluoromethylphenyl)methylene(3-tert-butyl-cyclopentadienyl)(3,6-divinylfluorenyl)zirconium dichloride, bis(p-fluorophenyl)methylene(3-tert-butyl-cyclopentadienyl)(3,6-divinylfluorenyl)zirconium dichloride, bis(m-fluorophenyl)methylene(3-tert-butyl-cyclopentadienyl)(3,6-divinylfluorenyl)zirconium dichloride, bis(p-chlorophenylmethylene)(3-tert-butyl-cyclopentadienyl)(3,6-divinylfluorenyl)zirconium dichloride, bis(m-chlorophenyl)methylene(3-tert-butyl-cyclopentadienyl)(3,6-divinylfluorenyl)zirconium dichloride, bis(p-tert-butylphenyl)methylene(3-tert-butyl-cyclopentadienyl)(3,6-divinylfluorenyl)zirconium dichloride, isopropylidene(3-tert-butyl-5-methylcyclopentadienyl)(3,6-divinylfluorenyl)zirconium dichloride, dibutylmethylene(3-tert-butyl-5-methylcyclopentadienyl)(3,6-divinylfluorenyl)zirconium dichloride, cyclohexylidene(3-tert-butyl-5-methylcyclopentadienyl)(3,6-divinylfluorenyl)zirconium dichloride, dibenzylmethylene(3-tert-butyl-5-methylcyclopentadienyl)(3,6-divinylfluorenyl)zirconium dichloride, phenylmethylene(3-tert-butyl-5-methylcyclopentadienyl)(3,6-divinylfluorenyl)zirconium dichloride, (phenyl)(methyl)methylene(3-tert-butyl-5-methylcyclopentadienyl)(3,6-divinylfluorenyl)zirconium dichloride, (p-tolyl)(methyl)methylene(3-tert-butyl-5-methylcyclopentadienyl)(3,6-divinylfluorenyl)zirconium dichloride, (phenyl)(ethyl)methylene(3-tert-butyl-5-methylcyclopentadienyl)(3,6-divinylfluorenyl)zirconium dichloride, diphenylmethylene(3-tert-butyl-5-methylcyclopentadienyl)(3,6-divinylfluorenyl)zirconium dichloride, di-p-tolylmethylene(3-tert-butyl-5-methylcyclopentadienyl)(3,6-divinylfluorenyl)zirconium dichloride, bis(p-trifluoromethylphenyl)methylene(3-tert-butyl-5-methyl cyclopentadienyl)(3,6-divinylfluorenyl)zirconium dichloride, bis(m-trifluoromethylphenyl)methylene(3-tert-butyl-5-methyl cyclopentadienyl)(3,6-divinylfluorenyl)zirconium dichloride, bis(p-fluorophenyl)methylene(3-tert-butyl-5-methylcyclopentadienyl)(3,6-divinylfluorenyl)zirconium dichloride, bis(m-fluorophenyl)methylene(3-tert-butyl-5-methylcyclopentadienyl)(3,6-divinylfluorenyl)zirconium dichloride, bis(p-chlorophenylmethylene)(3-tert-butyl-5-methylcyclopentadienyl)(3,6-divinylfluorenyl)zirconium dichloride, bis(m-chlorophenyl)methylene(3-tert-butyl-5-methylcyclopentadienyl)(3,6-divinylfluorenyl)zirconium dichloride, bis(p-tert-butylphenyl)methylene(3-tert-butyl-5-methylcyclopentadienyl)(3,6-divinylfluorenyl)zirconium dichloride, isopropylidene(3-tert-butyl-5-ethylcyclopentadienyl)(3,6-divinylfluorenyl)zirconium dichloride, dibutylmethylene(3-tert-butyl-5-ethylcyclopentadienyl)(3,6-divinylfluorenyl)zirconium dichloride, cyclohexylidene(3-tert-butyl-5-ethylcyclopentadienyl)(3,6-divinylfluorenyl)zirconium dichloride, dibenzylmethylene(3-tert-butyl-5-ethylcyclopentadienyl)(3,6-divinylfluorenyl)zirconium dichloride, phenylmethylene(3-tert-butyl-5-ethylcyclopentadienyl)(3,6-divinylfluorenyl)zirconium dichloride, (phenyl)(methyl)methylene(3-tert-butyl-5-ethylcyclopentadienyl)(3,6-divinylfluorenyl)zirconium dichloride, (p-tolyl)(methyl)methylene(3-tert-butyl-5-ethylcyclopentadienyl)(3,6-divinylfluorenyl)zirconium dichloride, (phenyl)(ethyl)methylene(3-tert-butyl-5-ethylcyclopentadienyl)(3,6-divinylfluorenyl)zirconium dichloride, diphenylmethylene(3-tert-butyl-5-ethylcyclopentadienyl)(3,6-divinylfluorenyl)zirconium dichloride, di-p-tolylmethylene(3-tert-butyl-5-ethylcyclopentadienyl)(3,6-divinylfluorenyl)zirconium dichloride, bis(p-trifluoromethylphenyl)methylene(3-tert-butyl-5-ethylcyclopentadienyl)(3,6-divinylfluorenyl)zirconium dichloride, bis(m-trifluoromethylphenyl)methylene(3-tert-butyl-5-ethylcyclopentadienyl)(3,6-divinylfluorenyl)zirconium dichloride, bis(p-fluorophenyl)methylene(3-tert-butyl-5-ethylcyclopentadienyl)(3,6-divinylfluorenyl)zirconium dichloride, bis(m-fluorophenyl)methylene(3-tert-butyl-5-ethylcyclopentadienyl)(3,6-divinylfluorenyl)zirconium dichloride, bis(p-chlorophenylmethylene)(3-tert-butyl-5-ethylcyclopentadienyl)(3,6-divinylfluorenyl)zirconium dichloride, bis(m-chlorophenyl)methylene(3-tert-butyl-5-ethylcyclopentadienyl)(3,6-divinylfluorenyl)zirconium dichloride, bis(p-tert-butylphenyl)methylene(3-tert-butyl-5-ethylcyclopentadienyl)(3,6-divinylfluorenyl)zirconium dichloride, isopropylidene(3,5-dimethylcyclopentadienyl)(3,6-divinylfluorenyl)zirconium dichloride, dibutylmethylene(3,5-dimethylcyclopentadienyl)(3,6-divinylfluorenyl)zirconium dichloride, cyclohexylidene(3,5-dimethylcyclopentadienyl)(3,6-divinylfluorenyl)zirconium dichloride, dibenzylmethylene(3,5-dimethylcyclopentadienyl)(3,6-divinyl fluorenyl)zirconium dichloride, phenylmethylene(3,5-dimethylcyclopentadienyl)(3,6-divinylfluorenyl)zirconium dichloride, (phenyl)(methyl)methylene(3,5-dimethylcyclopentadienyl)(3,6-divinylfluorenyl)zirconium dichloride, (p-tolyl)(methyl)methylene(3,5-dimethylcyclopentadienyl)(3,6-divinylfluorenyl)zirconium dichloride, (phenyl)(ethyl)methylene(3,5-dimethylcyclopentadienyl)(3,6-divinylfluorenyl)zirconium dichloride, diphenylmethylene(3,5-dimethylcyclopentadienyl)(3,6-divinyl fluorenyl)zirconium dichloride, di-p-tolylmethylene(3,5-dimethylcyclopentadienyl)(3,6-divinylfluorenyl)zirconium dichloride, bis(p-trifluoromethylphenyl)methylene(3,5-dimethylcyclopentadienyl)(3,6-divinylfluorenyl)zirconium dichloride, bis(m-trifluoromethylphenyl)methylene(3,5-dimethylcyclopentadienyl)(3,6-divinylfluorenyl)zirconium dichloride, bis(p-fluorophenyl)methylene(3,5-dimethylcyclopentadienyl)(3,6-divinylfluorenyl)zirconium dichloride, bis(m-fluorophenyl)methylene(3,5-dimethylcyclopentadienyl)(3,6-divinylfluorenyl)zirconium dichloride, bis(p-chlorophenylmethylene)(3,5-dimethylcyclopentadienyl)(3,6-divinylfluorenyl)zirconium dichloride, bis(m-chlorophenyl)methylene(3,5-dimethylcyclopentadienyl)(3,6-divinylfluorenyl)zirconium dichloride, bis(p-tert-butylphenyl)methylene(3,5-dimethylcyclopentadienyl)(3,6-divinylfluorenyl)zirconium dichloride, isopropylidene(cyclopentadienyl)(1,1,4,7,10,10-hexamethyl-1,2,9,10-tetrahydro-dibenzo[b,h]fluorenyl)zirconium dichloride, dibutylmethylene(cyclopentadienyl)(1,1,4,7,10,10-hexamethyl-1,2,9,10-tetrahydro-dibenzo[b,h]fluorenyl)zirconium dichloride, cyclohexylidene(cyclopentadienyl)(1,1,4,7,10,10-hexamethyl-1,2,9,10-tetrahydro-dibenzo[b,h]fluorenyl)zirconium dichloride, dibenzylmethylene(cyclopentadienyl)(1,1,4,7,10,10-hexamethyl-1,2,9,10-tetrahydro-dibenzo[b,h]fluorenyl)zirconium dichloride, phenylmethylene(cyclopentadienyl)(1,1,4,7,10,10-hexamethyl-1,2,9,10-tetrahydro-dibenzo[b,h]fluorenyl)zirconium dichloride, (phenyl)(methyl)methylene(cyclopentadienyl)(1,1,4,7,10,10-hexamethyl-1,2,9,10-tetrahydro-dibenzo[b,h]fluorenyl)zirconium dichloride, (p-tolyl)(methyl)methylene(cyclopentadienyl)(1,1,4,7,10,10-hexamethyl-1,2,9,10-tetrahydro-dibenzo[b,h]fluorenyl)zirconium dichloride, (phenyl)(ethyl)methylene(cyclopentadienyl)(1,1,4,7,10,10-hexamethyl-1,2,9,10-tetrahydro-dibenzo[b,h]fluorenyl)zirconium dichloride, diphenylmethylene(cyclopentadienyl)(1,1,4,7,10,10-hexamethyl-1,2,9,10-tetrahydro-dibenzo[b,h]fluorenyl)zirconium dichloride, di-p-tolylmethylene(cyclopentadienyl)(1,1,4,7,10,10-hexamethyl-1,2,9,10-tetrahydro-dibenzo[b,h]fluorenyl)zirconium dichloride, bis(p-trifluoromethylphenyl)methylene(cyclopentadienyl)(1,1,4,7,10,10-hexamethyl-1,2,9,10-tetrahydro-dibenzo[b,h]fluorenyl)zirconium dichloride, bis(m-trifluoromethylphenyl)methylene(cyclopentadienyl)(1,1,4,7,10,10-hexamethyl-1,2,9,10-tetrahydro-dibenzo[b,h]fluorenyl)zirconium dichloride, bis(p-fluorophenyl)methylene(cyclopentadienyl)(1,1,4,7,10,10-hexamethyl-1,2,9,10-tetrahydro-dibenzo[b,h]fluorenyl)zirconium dichloride, bis(m-fluorophenyl)methylene(cyclopentadienyl)(1,1,4,7,10,10-hexamethyl-1,2,9,10-tetrahydro-dibenzo[b,h]fluorenyl)zirconium dichloride, bis(p-chlorophenylmethylene)(cyclopentadienyl)(1,1,4,7,10,10-hexamethyl-1,2,9,10-tetrahydro-dibenzo[b,h]fluorenyl)zirconium dichloride, bis(m-chlorophenyl)methylene(cyclopentadienyl)(1,1,4,7,10,10-hexamethyl-1,2,9,10-tetrahydro-dibenzo[b,h]fluorenyl)zirconium dichloride, bis(p-tert-butylphenyl)methylene(cyclopentadienyl)(1,1,4,7,10,10-hexamethyl-1,2,9,10-tetrahydro-dibenzo[b,h]fluorenyl)zirconium dichloride, isopropylidene(3-tert-butyl-cyclopentadienyl)(1,1,4,7,10,10-hexamethyl-1,2,9,10-tetrahydro-dibenzo[b,h]fluorenyl)zirconium dichloride, dibutylmethylene(3-tert-butyl-cyclopentadienyl)(1,1,4,7,10,10-hexamethyl-1,2,9,10-tetrahydro-dibenzo[b,h]fluorenyl)zirconium dichloride, cyclohexylidene(3-tert-butyl-cyclopentadienyl)(1,1,4,7,10,10-hexamethyl-1,2,9,10-tetrahydro-dibenzo[b,h]fluorenyl)zirconium dichloride, dibenzylmethylene(3-tert-butyl-cyclopentadienyl)(1,1,4,7,10,10-hexamethyl-1,2,9,10-tetrahydro-dibenzo[b,h]fluorenyl)zirconium dichloride, phenylmethylene(3-tert-butyl-cyclopentadienyl)(1,1,4,7,10,10-hexamethyl-1,2,9,10-tetrahydro-dibenzo[b,h]fluorenyl)zirconium dichloride, (phenyl)(methyl)methylene(3-tert-butyl-cyclopentadienyl)(1,1,4,7,10,10-hexamethyl-1,2,9,10-tetrahydro-dibenzo[b,h]fluorenyl)zirconium dichloride, (p-tolyl)(methyl)methylene(3-tert-butyl-cyclopentadienyl)(1,1,4,7,10,10-hexamethyl-1,2,9,10-tetrahydro-dibenzo[b,h]fluorenyl)zirconium dichloride, (phenyl)(ethyl)methylene(3-tert-butyl-cyclopentadienyl)(1,1,4,7,10,10-hexamethyl-1,2,9,10-tetrahydro-dibenzo[b,h]fluorenyl)zirconium dichloride, diphenylmethylene(3-tert-butyl-cyclopentadienyl)(1,1,4,7,10,10-hexamethyl-1,2,9,10-tetrahydro-dibenzo[b,h]fluorenyl)zirconium dichloride, di-p-tolylmethylene(3-tert-butyl-cyclopentadienyl)(1,1,4,7,10,10-hexamethyl-1,2,9,10-tetrahydro-dibenzo[b,h]fluorenyl)zirconium dichloride, bis(p-trifluoromethylphenyl)methylene(3-tert-butyl-cyclopentadienyl)(1,1,4,7,10,10-hexamethyl-1,2,9,10-tetrahydro-dibenzo[b,h]fluorenyl)zirconium dichloride, bis(m-trifluoromethylphenyl)methylene(3-tert-butyl-cyclopentadienyl)(1,1,4,7,10,10-hexamethyl-1,2,9,10-tetrahydro-dibenzo[b,h]fluorenyl)zirconium dichloride, bis(p-fluorophenyl)methylene(3-tert-butyl-cyclopentadienyl)(1,1,4,7,10,10-hexamethyl-1,2,9,10-tetrahydro-dibenzo[b,h]fluorenyl)zirconium dichloride, bis(m-fluorophenyl)methylene(3-tert-butyl-cyclopentadienyl)(1,1,4,7,10,10-hexamethyl-1,2,9,10-tetrahydro-dibenzo[b,h]fluorenyl)zirconium dichloride, bis(p-chlorophenylmethylene)(3-tert-butyl-cyclopentadienyl)(1,1,4,7,10,10-hexamethyl-1,2,9,10-tetrahydro-dibenzo[b,h]fluorenyl)zirconium dichloride, bis(m-chlorophenyl)methylene(3-tert-butyl-cyclopentadienyl)(1,1,4,7,10,10-hexamethyl-1,2,9,10-tetrahydro-dibenzo[b,h]fluorenyl)zirconium dichloride, bis(p-tert-butylphenyl)methylene(3-tert-butyl-cyclopentadienyl)(1,1,4,7,10,10-hexamethyl-1,2,9,10-tetrahydro-dibenzo[b,h]fluorenyl)zirconium dichloride, isopropylidene(3-tert-butyl-5-methylcyclopentadienyl)(1,1,4,7,10,10-hexamethyl-1,2,9,10-tetrahydro-dibenzo[b,h]fluorenyl)zirconium dichloride, dibutylmethylene(3-tert-butyl-5-methylcyclopentadienyl)(1,1,4,7,10,10-hexamethyl-1,2,9,10-tetrahydro-dibenzo[b,h]fluorenyl)zirconium dichloride, cyclohexylidene(3-tert-butyl-5-methylcyclopentadienyl)(1,1,4,7,10,10-hexamethyl-1,2,9,10-tetrahydro-dibenzo[b,h]fluorenyl)zirconium dichloride, dibenzylmethylene(3-tert-butyl-5-methylcyclopentadienyl)(1,1,4,7,10,10-hexamethyl-1,2,9,10-tetrahydro-dibenzo[b,h]fluorenyl)zirconium dichloride, phenylmethylene(3-tert-butyl-5-methylcyclopentadienyl)(1,1,4,7,10,10-hexamethyl-1,2,9,10-tetrahydro-dibenzo[b,h]fluorenyl)zirconium dichloride, (phenyl)(methyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, (p-tolyl)(methyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, (phenyl)(ethyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, diphenylmethylene(3-tert-butyl-5-methylcyclopentadienyl)(1,1,4,7,10,10-hexamethyl-1,2,9,10-tetrahydro-dibenzo[b,h]fluorenyl)zirconium dichloride, di-p-tolylmethylene(3-tert-butyl-5-methylcyclopentadienyl)(1,1,4,7,10,10-hexamethyl-1,2,9,10-tetrahydro-dibenzo[b,h]fluorenyl)zirconium dichloride, bis(p-trifluoromethylphenyl)methylene(3-tert-butyl-5-methyl cyclopentadienyl)(1,1,4,7,10,10-hexamethyl-1,2,9,10-tetrahydro-dibenzo[b,h]fluorenyl)zirconium dichloride, bis(m-trifluoromethylphenyl)methylene(3-tert-butyl-5-methyl cyclopentadienyl)(1,1,4,7,10,10-hexamethyl-1,2,9,10-tetrahydro-dibenzo[b,h]fluorenyl)zirconium dichloride, bis(p-fluorophenyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, bis(m-fluorophenyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, bis(p-chlorophenylmethylene)(3-tert-butyl-5-methylcyclopentadienyl)(1,1,4,7,10,10-hexamethyl-1,2,9,10-tetrahydro-dibenzo[b,h]fluorenyl)zirconium dichloride, bis(m-chlorophenyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, bis(p-tert-butylphenyl)methylene(3-tert-butyl-5-methylcyclopentadienyl)(1,1,4,7,10,10-hexamethyl-1,2,9,10-tetrahydro-dibenzo[b,h]fluorenyl)zirconium dichloride, isopropylidene(3-tert-butyl-5-ethylcyclopentadienyl)(1,1,4,7,10,10-hexamethyl-1,2,9,10-tetrahydro-dibenzo[b,h]fluorenyl)zirconium dichloride, dibutylmethylene(3-tert-butyl-5-ethylcyclopentadienyl)(1,1,4,7,10,10-hexamethyl-1,2,9,10-tetrahydro-dibenzo[b,h]fluorenyl)zirconium dichloride, cyclohexylidene(3-tert-butyl-5-ethylcyclopentadienyl)(1,1,4,7,10,10-hexamethyl-1,2,9,10-tetrahydro-dibenzo[b,h]fluorenyl)zirconium dichloride, dibenzylmethylene(3-tert-butyl-5-ethylcyclopentadienyl)(1,1,4,7,10,10-hexamethyl-1,2,9,10-tetrahydro-dibenzo[b,h]fluorenyl)zirconium dichloride, phenylmethylene(3-tert-butyl-5-ethylcyclopentadienyl)(1,1,4,7,10,10-hexamethyl-1,2,9,10-tetrahydro-dibenzo[b,h]fluorenyl)zirconium dichloride, (phenyl)(methyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, (p-tolyl)(methyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, (phenyl)(ethyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, diphenylmethylene(3-tert-butyl-5-ethylcyclopentadienyl)(1,1,4,7,10,10-hexamethyl-1,2,9,10-tetrahydro-dibenzo[b,h]fluorenyl)zirconium dichloride, di-p-tolylmethylene(3-tert-butyl-5-ethylcyclopentadienyl)(1,1,4,7,10,10-hexamethyl-1,2,9,10-tetrahydro-dibenzo[b,h]fluorenyl)zirconium dichloride, bis(p-trifluoromethylphenyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, bis(m-trifluoromethylphenyl)methylene(3-tert-butyl-5-ethylcyclopentadienyl)(1,1,4,7,10,10-hexamethyl-1,2,9,10- tetrahydro-dibenzo[b,h]fluorenyl)zirconium dichloride, bis(p-fluorophenyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, bis(m-fluorophenyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, bis(p-chlorophenylmethylene)(3-tert-butyl-5-ethylcyclopentadienyl)(1,1,4,7,10,10-hexamethyl-1,2,9,10-tetrahydro-dibenzo[b,h]fluorenyl)zirconium dichloride, bis(m-chlorophenyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, bis(p-tert-butylphenyl)methylene(3-tert-butyl-5-ethylcyclopentadienyl)(1,1,4,7,10,10-hexamethyl-1,2,9,10-tetrahydro-dibenzo[b,h]fluorenyl)zirconium dichloride, isopropylidene(3,5-dimethylcyclopentadienyl)(1,1,4,7,10,10-hexamethyl-1,2,9,10-tetrahydro-dibenzo[b,h]fluorenyl)zirconium dichloride, dibutylmethylene(3,5-dimethylcyclopentadienyl)(1,1,4,7,10,10-hexamethyl-1,2,9,10-tetrahydro-dibenzo[b,h]fluorenyl)zirconium dichloride, cyclohexylidene(3,5-dimethylcyclopentadienyl)(1,1,4,7,10,10-hexamethyl-1,2,9,10-tetrahydro-dibenzo[b,h]fluorenyl)zirconium dichloride, dibenzylmethylene(3,5-dimethylcyclopentadienyl)(1,1,4,7,10,10-hexamethyl-1,2,9,10-tetrahydro-dibenzo[b,h]fluorenyl)zirconium dichloride, phenylmethylene(3,5-dimethylcyclopentadienyl)(1,1,4,7,10,10-hexamethyl-1,2,9,10-tetrahydro-dibenzo[b,h]fluorenyl)zirconium dichloride, (phenyl)(methyl)methylene(3,5-dimethylcyclopentadienyl)(1,1,4,7,10,10-hexamethyl-1,2,9,10-tetrahydro-dibenzo[b,h]fluorenyl)zirconium dichloride, (p-tolyl)(methyl)methylene(3,5-dimethylcyclopentadienyl)(1,1,4,7,10,10-hexamethyl-1,2,9,10-tetrahydro-dibenzo[b,h]fluorenyl)zirconium dichloride, (phenyl)(ethyl)methylene(3,5-dimethylcyclopentadienyl)(1,1,4,7,10,10-hexamethyl-1,2,9,10-tetrahydro-dibenzo[b,h]fluorenyl)zirconium dichloride, diphenylmethylene(3,5-dimethylcyclopentadienyl)(1,1,4,7,10,10-hexamethyl-1,2,9,10-tetrahydro-dibenzo[b,h]fluorenyl)zirconium dichloride, di-p-tolylmethylene(3,5-dimethylcyclopentadienyl)(1,1,4,7,10,10-hexamethyl-1,2,9,10-tetrahydro-dibenzo[b,h]fluorenyl)zirconium dichloride, bis(p-trifluoromethylphenyl)methylene(3,5-dimethylcyclopentadienyl)(1,1,4,7,10,10-hexamethyl-1,2,9,10-tetrahydro-dibenzo[b,h]fluorenyl)zirconium dichloride, bis(m-trifluoromethylphenyl)methylene(3,5-dimethylcyclopentadienyl)(1,1,4,7,10,10-hexamethyl-1,2,9,10-tetrahydro-dibenzo[b,h]fluorenyl)zirconium dichloride, bis(p-fluorophenyl)methylene(3,5-dimethylcyclopentadienyl)(1,1,4,7,10,10-hexamethyl-1,2,9,10-tetrahydro-dibenzo[b,h]fluorenyl)zirconium dichloride, bis(m-fluorophenyl)methylene(3,5-dimethylcyclopentadienyl)(1,1,4,7,10,10-hexamethyl-1,2,9,10-tetrahydro-dibenzo[b,h]fluorenyl)zirconium dichloride, bis(p-chlorophenylmethylene)(3,5-dimethylcyclopentadienyl)(1,1,4,7,10,10-hexamethyl-1,2,9,10-tetrahydro-dibenzo[b,h]fluorenyl)zirconium dichloride, bis(m-chlorophenyl)methylene(3,5-dimethylcyclopentadienyl)(1,1,4,7,10,10-hexamethyl-1,2,9,10-tetrahydro-dibenzo[b,h]fluorenyl)zirconium dichloride and bis(p-tert-butylphenyl)methylene(3,5-dimethylcyclopentadienyl)(1,1,4,7,10,10-hexamethyl-1,2,9,10-tetrahydro-dibenzo[b,h]fluorenyl)zirconium dichloride. However, the transition metal compound of the present invention is not limited to the above-exemplified compounds, and examples thereof include all the compounds satisfying the requirements as described in the claims.

In the present invention, there may be also employed, without any limitation, a derivative in which a carbon-carbon double bond contained in the skeleton of the substituent(s) at the 3-position and/or the 6-position of the fluorene derivative represented by the general formula [I] is chemically modified by a well-known method, for example, a derivative in which a carbon-carbon double bond is epoxidized by a peracid and the like, a derivative in which the epoxidized derivative is subjected to ring-opening with an active hydrogen-containing compound, and the like, as long as the polymerization activity of the invention can be exhibited.

Process for Producing Fluorene Derivative

The fluorene derivative of the present invention can be produced by a well-known method, and the process for producing the same is not particularly limited. Examples of the well-known production process include the process as disclosed in WO01/27124, filed by the present Applicant. First, a precursor compound (I) of the general formula [I] can be produced by the reaction scheme [A].

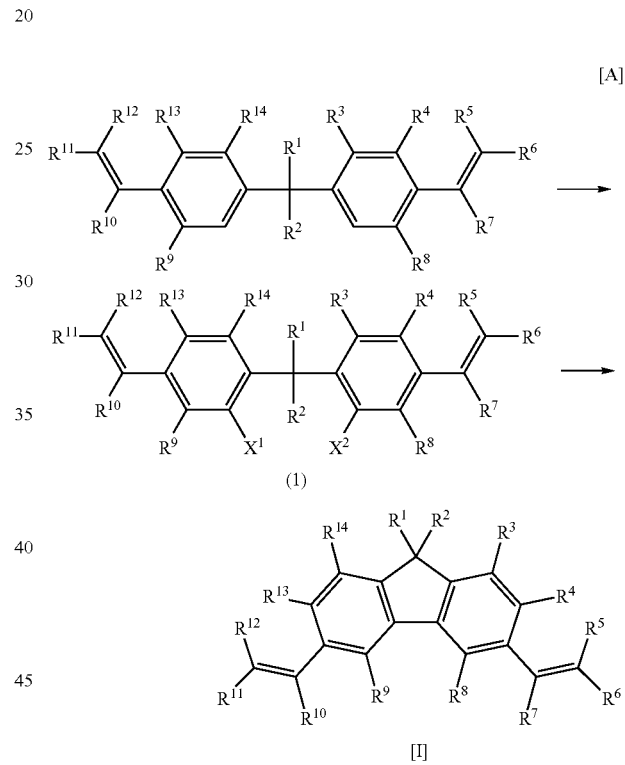

In the formula, $R^1$ to $R^{14}$ each have the same meanings as in the general formula [I], and $X^1$ and $X^2$ each represent a halogen atom, a trifluoromethylsulfonate group, a sulfonate group, or the like, which may be the same as or different from each other. By coupling the compound of the formula (1) in accordance with a well-known method, a compound of the general formula [I] can be obtained. The coupling reaction can be carried out in the absence or presence of an organic solvent, at temperature ranging from −80° C. to 300° C., by using at least one selected from a transition metal compound obtained by adding a ligand if necessary to a nickel salt such as nickel chloride, nickel nitrate, a palladium salt such as palladium chloride, palladium acetate, in addition to a metal such as copper, magnesium, zinc, lithium, sodium, and potassium, and an organometallic compound such as alkyllithium, alkylmagnesium halide, and arylmagnesium halide.

In addition, the compound of the general formula [II] can be produced by the reaction scheme [B].

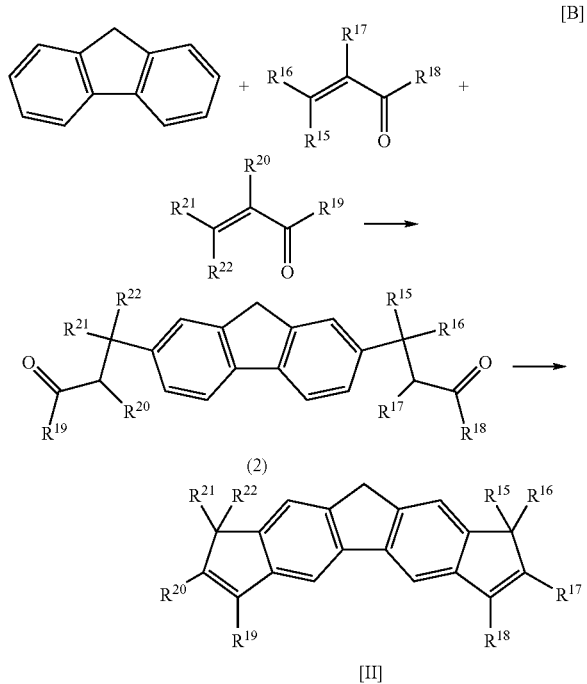

In the formula, $R^{15}$ to $R^{22}$ each have the same meanings as in the general formula [II]. The synthesis of the compound represented by the formula (2), which is an intermediate, is carried out in the absence or presence of organic solvent, at the temperature ranging from −100° C. to 200° C., by using fluorene and well-known α,β-unsaturated ketones as a raw material, and in the presence of the catalyst, if necessary. α,β-unsaturated ketone as a raw material is not particularly limited, but include, for example, but-3-en-2-one, pent-3-en-2-one, 4-methyl-pent-3-en-2-one, 4-phenyl-but-3-en-2-one, 1-phenylpropenone, 1,3-diphenylpropenone, 2-methylpropenone, 2,4-dimethyl-pent-3-en-2-one, 4,4-dimethyl-pent-1-en-3-one, 2,2-dimethyl-hex-4-en-3-one, 2,2,5-trimethyl-hex-4-en-3-one. These may be used 1 to 20 equivalences, preferably 1.8 to 10 equivalences, and more preferably 2 to 5 equivalences, relative to fluorene. The solvent is not particularly limited, but the reaction may be carried out in the absence of a solvent or in the presence of a solvent such as dichloromethane, chloroform, carbon tetrachloride, chlorobenzene, dichlorobenzene, nitrobenzene, nitromethane, carbondisulfide, hexane, heptane, decane, and cyclohexane. The catalyst may be added to the reaction, if necessary. As the catalyst, one or more of a well-known Lewis acid such as hydrochloric acid, hydrogen chloride, sulfuric acid, nitric acid, phosphoric acid, polyphosphoric acid, diphosphorus pentaoxide, trifluoromethanesulfonic acid, methanesulfonic acid, hydrofluoric acid, aluminum chloride, stannic chloride, ferric chloride, zinc chloride, boron fluoride, cupric chloride, mercury chloride, titanium tetrachloride, zirconium tetrachloride, hafnium tetrachloride, aluminum bromide, ferric bromide, beryllium chloride, and zinc, gallium chloride, and a solid acid such as heteropoly acid, alumina, and zeolite may be employed.

The synthesis of the fluorene derivative represented by the general formula [II] from the intermediate represented by the formula (2) may be carried out in the same manner as the synthesis of the intermediate represented by the formula (2). The intermediate (2) may be isolated, but may derive the fluorene derivative represented by the general formula [II] directly without being isolated.

Process for Producing Transition Metal Compound

The transition metal compound of the present invention can be produced by a well-known method, and the process for producing the same is not particularly limited. Examples of the well-known production process include the process as disclosed in WO01/27124, filed by the present Applicant. For example, the compound represented by the general formula [III] can be produced by the following steps. Firstly, the precursor compound (9) of the general formula [III] can be produced by the reaction scheme [C] or [D].

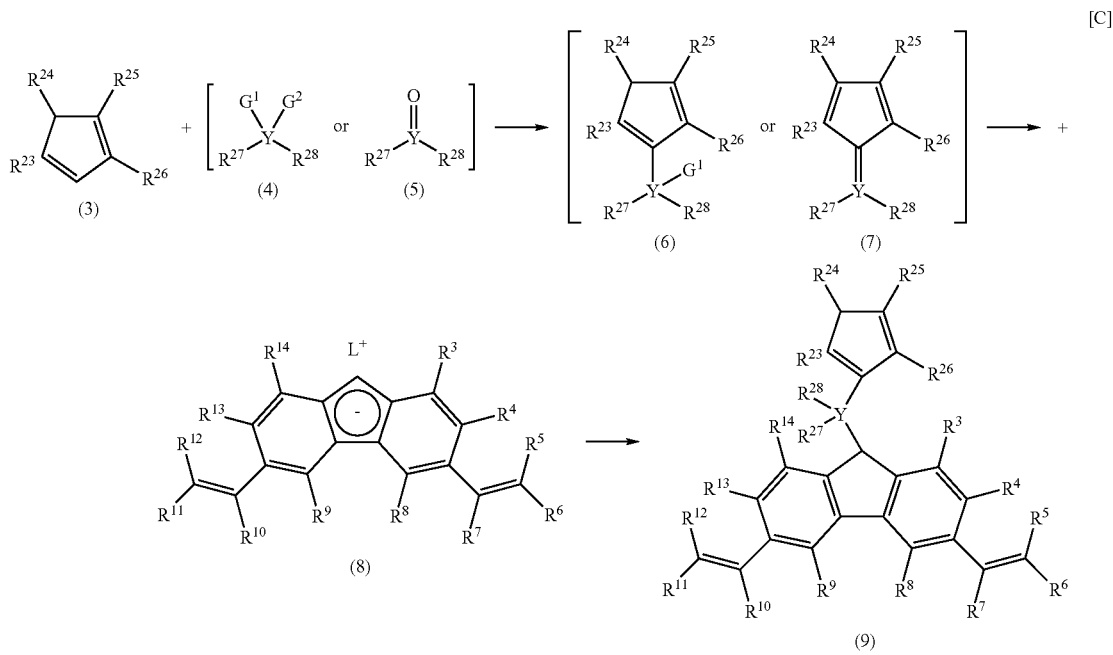

-continued

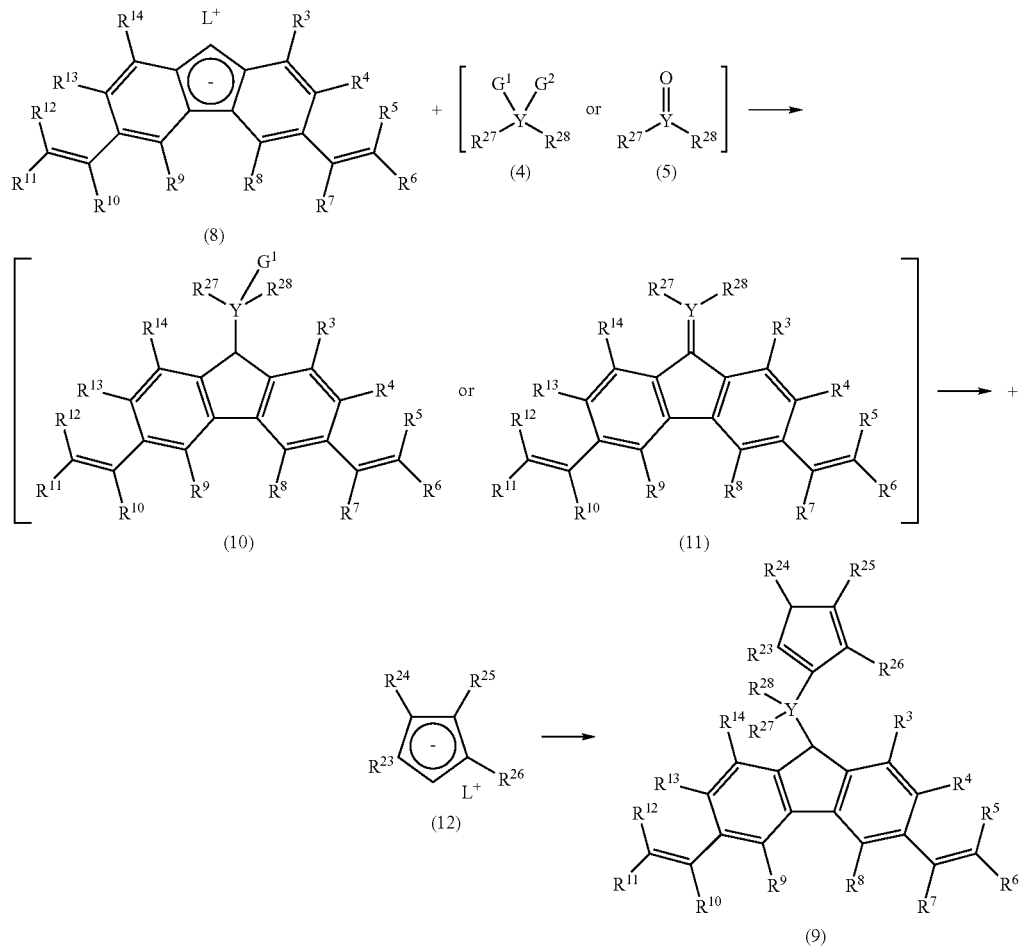

In the formula, $R^3$ to $R^{26}$, and Y have the same meanings as in the general formula [I] and [III], and L represents an alkali metal. $G^1$ and $G^2$ each represent halogen or an anionic ligand, and these may be in the same or different combination. For (1), (2), and (5), it can be thought that there exist isomers which differ only in the position of a double bond in the cyclopentadienyl ring and only the one type among them is exemplified herein, but there may be any other isomers which differ only in the position of a double bond in the cyclopentadienyl ring, or a mixture thereof.

The alkali metal used for the reaction of the reaction schemes [C] and [D] may be lithium, sodium, or potassium, and the alkaline earth metal may be magnesium, or calcium. In addition, halogen may be fluorine, chlorine, bromine, or iodine. Specific examples of the anionic ligand include an alkoxy group such as methoxy, tert-butoxy, and phenoxy, a carboxylate group such as acetate, and benzoate, and a sulfonate such as mesilate and tosilate.

Next, examples of producing a transition metal compound from the precursor compound of the general formula (9) are listed below, but do not limit the scope of the invention. Further, the transition metal compound may be produced by any well-known method. The precursor compound of the general formula (9) obtained by the reaction of the reaction schemes [C] and [D] is brought into contact with an alkali metal, a hydrogenated alkali metal, or an organoalkali metal in an organic solvent at a reaction temperature ranging from −80° C. to 200° C., to obtain dialkali metal salt. Examples of the organic solvent used in the above reaction include aliphatic hydrocarbons such as pentane, hexane, heptane, cyclohexane, and decalin, aromatic hydrocarbons such as benzene, toluene and xylene, ethers such as tetrahydrofuran, diethylether, dioxane, 1,2-dimethoxyethane, tert-butylmethylether, and cyclopentylmethylether, and halogenated hydrocarbons such as dichloromethane and chloroform. In addition, examples of the alkali metal used in the above reaction include lithium, sodium, and potassium, examples of the hydrogenated alkali metal include sodium hydride, and potassium hydride, and examples of the organoalkali metal include methyllithium, butyllithium, and phenyllithium.

Next, the metallocene compound represented by the general formula [III] can be synthesized by reacting the obtained dialkali metal salt in the organic solvent with the compound represented by the general formula (13):

$$MJk \quad (13)$$

(In the formula, M represents a metal selected from Group 4 in the Periodic Table, J may be selected from the same or different combinations of halogen, an anionic ligand, or a neutral ligand capable of coordination with a lone electron pair, and k represents an integer of 3 to 6.). Specific examples of the preferable compound represented by the general formula (13) may include trivalent or tetravalent titanium fluoroide, chloride, bromide, and iodide, tetravalent zirconium fluororide, chloride, bromide, and iodide, tetravalent hafnium fluororide, chloride, bromide, and iodide, and complex thereof with ether such as tetrahydrofuran, diethylether, dioxane, and 1,2-dimethoxyethan. In addition, the organic solvent used may be the same ones as mentioned above. The reaction of the obtained dialkali metal salt with the compound represented by the general formula (13) may be preferably carried out by the equimolar reaction, and may be carried out in the above-mentioned organic solvent at a reaction temperature ranging from −80° C. to 200° C. The metallocene compound obtained in the reaction may be isolated and purified in accordance with the process such as an extraction, a recrystallization, a sublimation, and the like. The transition metal compound of the present invention obtained by the process is identified using the analytical method such as a proton nuclear magnetic resonance spectrum, a $^{13}$C nuclear magnetic resonance spectrum, a mass analysis, and an elemental analysis.

Preferred Embodiment of Employing Transition Metal Compound to Catalyst for Olefin Polymerization Next, the preferred embodiment of employing the transition metal compound of the present invention to a catalyst for olefin polymerization will be explained. In the case of using the transition metal compound of the present invention as the catalyst for olefin polymerization, the catalyst component preferably comprises:

(A) the above-mentioned transition metal compound;
(B) at least one compound selected from:
(B-1) an organometallic compound,
(B-2) an organoaluminum oxy-compound, and
(B-3) a compound which forms an ion pair by reacting with the transition metal compound (A); and further, if necessary,
(C) a particulate carrier.

Hereinafter, each component will be specifically explained.

(B-1) Organometallic Compound

Examples of organometallic compound (B-1) used in the present invention, specifically include the following organometallic compounds of Groups 1, 2, 12 and 13.

An organoaluminum compound represented by the general formula:

$$R^a{}_mAl(OR^b)_nH_pE_q \qquad \text{General Formula (B-1a)}$$

wherein Ra and Rb may be the same or different and each represent a hydrocarbon group having 1 to 15, preferably 1 to 4 carbon atoms; E represents a halogen atom; m is a number such that $0<m\leqq 3$, n is a number such that $0\leqq n<3$, p is a number such that $0\leqq p<3$, and q is a number such that $0\leqq q<3$, provided that m+n+p+q=3. The specific examples of the compound include trimethylaluminum, triethylaluminum, triisobutylaluminum, and diisobutylaluminum hydride.

An alkyl complex of Group 1 metal and aluminum represented by the general formula:

$$M^2AlR^a{}_4 \qquad \text{General Formula (B-1b)}$$

wherein $M^2$ represents Li, Na, or K, $R^a$ represents a hydrocarbon group having 1 to 15, preferably 1 to 4 carbon atom(s). Examples of the compound include LiAl(C$_2$H$_5$)$_5$, and LiAl(C$_7$H$_{15}$)$_4$.

A dialkyl compound of Group 2 or 12 metal represented by the general formula:

$$R^aR^bM^3 \qquad \text{General Formula (B-1c)}$$

wherein $R^a$ and $R^b$ may be the same or different and each represent a hydrocarbon group having 1 to 15, preferably 1 to 4 carbon atoms, $M^3$ represents Mg, Zn, or Cd. Among the above-mentioned organometallic compounds (B-1), organoaluminum compound is preferable. In addition, such organometallic compound (B-1) may be used individually or in a combination of two or more kinds thereof.

(B-2) Organoaluminum Oxy-Compound

An organoaluminum oxy-compound (B-2) used in the present invention may be a well-known aluminoxane or an organoaluminum oxy-compound which is insoluble to benzene as disclosed in Japanese Unexamined Patent Application Publication No. H2-78687.

The heretofore known aluminoxane may be produced in accordance with, for example, the following processes, and generally obtained as a solution of hydrocarbon solvent.

(1) Process which comprises adding an organoaluminum compound such as trialkylaluminum to a compound containing an adsorptive water or salts containing crystal water, for example, a magnesium chloride hydrate, a copper sulfate hydrate, an aluminum sulfate hydrate, a nickel sulfate hydrate, and a cerium chloride hydrate in a hydrocarbon medium suspension, so as to react the adsorptive water or the crystal water with the organoaluminum compound.

(2) Process which comprises directly reacting water, ice or steam with an organoaluminum compound such as trialkylaluminum, in a medium such as benzene, toluene, diethylether, and tetrahydrofuran.

(3) Process which comprises reacting an organic tin oxide such as dimethyl tin oxide and dibutyl tin oxide, with an organoaluminum compound such as trialkylaluminum, in a medium such as decane, benzene, and toluene.

The aluminoxane may contain a small amount of an organometallic component. From the recovered solution of aluminoxane, a solvent or unreacted organoaluminum compound is distilled off, and subsequently the resultant may be re-dissolved in a solvent or suspended in a poor solvent of aluminoxane. Examples of the organoaluminum compound used for the preparation of the aluminoxane can specifically include the same organoaluminum compound as those exemplified as the organoaluminum compound in the above-mentioned (B-1a). Among these, trialkylaluminum and tricycloalkylaluminum are preferable, and trimethylaluminum is particularly preferable. The organoaluminum compound may be used individually or in a combination of two or more kinds thereof.

In addition, the organoaluminum oxy-compound which is insoluble to benzene used in the present invention is preferably a compound having an Al component, which is soluble to benzene at 60° C. of generally 10% or less, preferably 5% or less, particularly preferably 2% or less in terms of Al atoms, that is, a compound which is insoluble or hardly soluble to benzene. The organoaluminum compound (B-2) may be used individually or in a combination of two or more kinds thereof.

(B-3) Compound which Forms Ion Pair by Reacting with Transition Metal Compound

Examples of the compound which forms an ion pair by reacting with the transition metal compound (A) used in the present invention (B-3) (hereinafter referred to as 'ionizing ionic compound') include a Lewis acid, an ionic compound, a borane compound, and a carborane compound as disclosed in Japanese Unexamined Patent Application Publication Nos. H1-501950, H1-502036, H3-179005, H3-179006, H3-207703, H3-207704, and U.S. Pat. No. 5,321,106, etc. Furthermore, a heteropoly compound and an isopoly compound may be exemplified. The ionizing ionic compound (B-3) may be used individually or in a combination of two or more kinds thereof. In the case of using the transition metal compound of the present invention as a catalyst for olefin polymerization, together with the organoaluminum oxy-compound (B-2) such as methylaminoxane as a co-catalyst component, gives especially high polymerization activity for the olefin compound.

Moreover, the catalyst for olefin polymerization according to the present invention may include a carrier (C), if necessary, together with the transition metal compound (A), at least one compound (B) selected from (B-1) an organometallic compound, (B-2) an organoaluminum oxy-compound, and (B-3) an ionizing ionic compound.

(C) Carrier

The carrier (C) used in the present invention is a solid in the form of granules or microparticles consisting of an inorganic or organic compound. Among such compounds, preferred as the inorganic compound are porous oxides, inorganic chlorides, clay, clay minerals or ion exchangeable layer compounds.

As the porous oxides, specifically, $SiO_2$, $Al_2O_3$, MgO, $ZrO_2$, $TiO_2$, $B_2O_3$, CaO, ZnO, BaO, $ThO_2$ and the like, or a complex or a mixture thereof, for example, a natural or synthetic zeolite, $SiO_2$—MgO, $SiO_2$—$Al_2O_3$, $SiO_2$—$TiO_2$, $SiO_2$—$V_2O_5$, $SiO_2$—$Cr_2O_3$, $SiO_2$—$TiO_2$—MgO and the like, can be used. Among these, $SiO_2$ and/or $Al_2O_3$ as a main component are/is preferably used. The porous oxide has different properties depending on the kind and the production method thereof. It is desirable that the carrier preferably used in the present invention has a particular diameter of 5 to 300 μm, more preferably 10 to 100 μm, a specific surface area of 50 to 1000 $m^2/g$, more preferably from 200 to 900 $m^2/g$, and a pore volume of 0.3 to 3.0 $cm^3/g$. The carrier may be calcined to be used at 100 to 1000° C., preferably 150 to 700° C., if necessary.

As the inorganic chlorides, $MgCl_2$, $MgBr_2$, $MnCl_2$, $MnBr_2$ and the like are used. The inorganic chlorides may be used directly, or may be used after being pulverized by using a ball mill or a vibrating mill. In addition, the inorganic chlorides can be used after dissolving them in a solvent such as alcohol, and then precipitating them into particulates using a precipitating agent.

The clay used in the present invention generally constitutes a clay mineral as the main component. The ion exchangeable layer compound used in the present invention is a compound having a crystal structure of which the planes constituted by ionic bonding are piled up to one another in parallel with a weak bonding strength, in which the ions contained can be exchanged. Most of the clay minerals are an ion exchangeable layer compound. For clays, clay minerals and ion exchangeable layer compounds, ones synthesized artificially can also be used without being limited to the natural products. In addition, examples of the clay, clay mineral, and ion exchangeable layer compound include clays, clay minerals, and crystalline ion compounds having a layered crystal structure such as a hexagonal close-packed structure, antimonyl type, $CdCl_2$ type, and $CdI_2$ type. Examples of the clay and clay mineral include kaolin, bentonite, kibushi clay, gairome clay, allophone, hisingerite, pyrophyllite, mica group, montmorillonite group, vermiculite, phyllite group, palygorskite, kaolinite, nacrite, dickite, halloysite, and the like. Examples of the ion exchangeable layer compound include a crystalline acid salt of multivalent metal such as α-$Zr(HAsO_4)_2 \cdot H_2O$, α-$Zr(HPO_4)_2$, α-$Zr(KPO_4)_2 \cdot 3H_2O$, α-$Ti(HPO_4)_2$, α-$Ti(HAsO_4)_2 \cdot H_2O$, α-$Sn(HPO_4)_2 \cdot H_2O$, γ-$Zr(HPO_4)_2$, γ-$Ti(HPO_4)_2$, γ-$Ti(NH_4PO_4)_2 \cdot H_2O$, and the like. The clay and clay mineral used in the present invention are preferably subjected to a chemical treatment. Any of the chemical treatment such as a surface treatment which removes impurities attached on the surface, treatments giving an effect on the crystal structure of the clay and the like, can be used. Specific examples of the chemical treatment include an acid treatment, an alkali treatment, a treatment with salts, a treatment with organic compound and the like.

The ion exchangeable layer compound used in the present invention may be a layer compound with the interlayer enlarged by exchanging an exchangeable ion inside the layer to the other bulky ion using its ion exchangeability. Such bulky ion plays a supportive role to support a layer structure, and is generally called as a pillar. Also, the introduction of other substance to the inside layer of the layer compound is known as the intercalation. Examples of the guest compound for intercalation include a positive ion inorganic compound such as $TiCl_4$ and $ZrCl_4$, a metal alkoxide (where R is a hydrocarbon group or the like) such as $Ti(OR)_4$, $Zr(OR)_4$, $PO(OR)_3$, and $B(OR)_3$, a metal hydroxide ion such as $[Al_{13}O_4(OH)_{24}]$, $[Zr_4(OH)_{14}]$, $[Fe_3O(OCOCH_3)_6]^+$, and the like. These compounds may be used individually or in a combination of two or more kinds thereof. In addition, when intercalating those compounds, a polymer obtained by hydrolyzing metal alkoxide (R is a hydrocarbon group, or the like) such as $Si(OR)_4$, $Al(OR)_3$ or $Ge(OR)_4$, a colloidal inorganic compound such as $SiO_2$ or the like can be coexisted. Examples of the pillar include an oxide produced by carrying out thermal dehydration after intercalating the above-mentioned metal hydroxide ion to the layer inside. Among these, preferred ones are clay and clay mineral, and specifically preferred ones are montmorillonite, vermiculite, pectorite, tainiolite, and synthetic mica.

Examples of the organic compound include a granule or a particulate solid having a particular diameter in the range of 5 to 300 μm. Specific examples thereof include a (co)polymer produced from an α-olefin having 2 to 14 carbon atoms such as ethylene, propylene, 1-butene, and 4-methyl-1-pentene as the main component; a (co)polymer produced from vinylcyclohexane, styrene as the main component; and a modified one thereof.

The catalyst for olefin polymerization according to the present invention may contain a carrier (C) and a specific organic compound component (D) to be described later, if necessary, together with the transition metal compound (A), at least one compound (B) selected from (B-1) an organometallic compound, (B-2) an organoaluminum oxy-compound, and (B-3) an ionizing ionic compound.

(D) Organic Compound Component

In the present invention, the organic compound component (D) is used, if necessary, for the purpose of improving the polymerization performance and properties of the produced polymer. Examples of the organic compound include alcohols, phenolic compounds, carboxylic acids, phosphorous compounds, and sulfonates, but are not limited thereto.

At the time of polymerization, the type of usage of each component and the adding sequence of each component can be arbitrarily selected, and the following processes can be exemplified.

(1) A process comprising adding the component (A) alone to a polymerization reactor.

(2) A process comprising adding the component (A) and the component (B) to a polymerization reactor in the arbitrary order.

(3) A process comprising adding the catalyst component in which the component (A) supported on the carrier (C), and the component (B) to a polymerization reactor in the arbitrary order.

(4) A process comprising adding the catalyst component in which the component (B) supported on the carrier (C), and the component (A) to a polymerization reactor in the arbitrary order.

(5) A process comprising adding the catalyst component in which the component (A) and the component (B) both supported on the carrier (C), to a polymerization reactor.

In each of the above-mentioned processes (2) to (5), at least two of each catalyst components may be contacted in advance. In each of the above-mentioned processes (4) and (5), of which the component (B) is supported, the component (B) that is not supported may be added in the arbitrary order, if necessary. In this case, the component (B) may either be the same as or different from each other. As the solid catalyst component in which the component (A) is supported on the above-mentioned component (C), and the solid catalyst component in which the component (A) and the component (B) are supported on the above-mentioned component (C), olefin may be prepolymerized, and further the catalyst component may be supported on the solid catalyst component which is prepolymerized.

In the process for producing an olefin polymer according to the present invention, an olefin polymer is obtained by polymerizing or copolymerizing the olefin in the presence of such catalyst for olefin polymerization as mentioned above. In the present invention, the polymerization can be carried out in any of a liquid-phase polymerization method such as a solution polymerization and a suspension polymerization, and a gas-phase polymerization method. Specific examples of the inactive hydrocarbon medium used in the liquid-phase polymerization method include aliphatic hydrocarbons such as propane, butane, pentane, hexane, heptane, octane, decane, dodecane and kerosene; alicyclic hydrocarbons such as cyclopentane, cyclohexaneandmethylcyclopentane; aromatic hydrocarbons such as benzene, toluene, and xylene; halogenated hydrocarbons such as ethylene chloride, chlorobenzene, and dichloromethane; and a mixture thereof. Also, olefin itself can be used as the solvent.

When the olefin polymerization is carried out by using such the olefin polymerization catalyst as mentioned above, the component (A) is used in such an amount so as to be generally from $10^{-8}$ to $10^{-2}$ mole, and preferably from $10^{-7}$ to $10^{-3}$ mole per a reaction volume of 1 L. The component (B-1) is used in such the amount that the molar ratio [(B-1)/M] of the component (B-1) to the entire transition metal (M) in the component (A) is generally from 0.01 to 5,000, and preferably from 0.05 to 2,000. The component (B-2) is used in such the amount that the molar ratio [(B-2)/M] of an aluminum atom in the component (B-2) to the entire transition metal (M) in the component (A) is generally from 10 to 5,000, preferably from 20 to 2,000. The component (B-3) is used in such the amount that the molar ratio [(B-3)/M] of the component (B-3) to the entire transition metal atom (M) in the component (A) is generally from 1 to 10, preferably from 1 to 5.

The component (D) is used in the amount such that the molar ratio [(D)/(B-1)] is generally from 0.01 to 10, preferably from 0.1 to 5 when the component (B) is the component (B-1), that the molar ratio [(D)/(B-2)] is generally from 0.01 to 2, preferably from 0.005 to 1 when the component (B) is the component (B-2), and that the molar ratio [(D)/(B-3)] is generally from 0.01 to 10, preferably from 0.1 to 5 when the component (B) is the component (B-3).

In addition, the polymerization temperature of olefin using the olefin polymerization catalyst is generally within the range from −50 to +200° C., and preferably from 0 to 170° C. The polymerization pressure is under the condition of generally from atmospheric pressure to 10 MPa gauge pressure, preferably from atmospheric pressure to 5 MPa gauge pressure, and the polymerization reaction can be carried out batchwise, semicontinuously or continuously. The polymerization can be carried out by dividing the process into two or more stages which use different reaction conditions. The molecular weight of the obtained olefin polymer can be also adjusted by allowing hydrogen to exist in the polymerization system, or by varying the polymerization temperature. Moreover, the molecule weight can be adjusted according to the amount of the component (B) used. When adding hydrogen, a suitable amount to be added is from about 0.001 to 100 NL per kg of olefin.

In the present invention, the olefin supplied to a polymerization reaction is at least one kind of monomer selected from ethylene and an α-olefin in which at least one kind of monomer is preferably ethylene or propylene. Examples of the α-olefin include a linear chain or branched α-olefin having 3 to 20 carbon atoms, preferably 3 to 10 carbon atoms, such as propylene, 1-butene, 2-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, and 1-eicosene. Additionally, examples of the α-olefin include a cyclic olefin having 3 to 30 carbon atoms, preferably 3 to 20 atoms, such as cyclopentene, cycloheptene, norbornene, 5-methyl-2-norbornene, tetracyclododecene and 2-methyl 1,4,5,8-dimethano-1,2,3,4,4a,5,8,8a-octahydronaphthalene; a polar monomer, for example, an α,β-unsaturated carboxylic acid such as acrylic acid, methacrylic acid, fumaric acid, maleic acid anhydride, itaconic acid, itaconic acid anhydride and bicyclo(2,2,1)-5-heptene-2,3-dicarboxylic anhydride, and a metal salt thereof such as sodium salt, potassium salt, lithium salt, zinc salt, magnesium salt, calcium salt and aluminum salt; an α,β-unsaturated carboxylic ester such as methyl acrylate, ethyl acrylate, n-propyl acrylate, isopropyl acrylate, n-butyl acrylate, isobutyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate; a vinylester such as vinyl acetate, vinyl propionate, vinyl caproate, vinyl caprate, vinyl laurate, vinyl stearate and vinyl trifluoroacetate; an unsaturated glycidyl such as glycidyl acrylate, glycidyl methacrylate, monoglycidyl itaconate. Furthermore, vinylcyclohexane, diene, polyene and aromatic vinyl compound, for example, styrene and monoalkylstyrene or polyalkylstyrene such as o-methylstyrene, m-methylstyrene, p-methylstyrene, o,p-dimethylstyrene, o-ethylstyrene, m-ethylstyrene, p-ethylstyrene; a styrene derivative containing a functional group such as methoxy styrene, ethoxy styrene, vinyl benzoate, vinyl methylbenzoate, vinyl benzyl acetate, hydroxy styrene, o-chlorostyrene, p-chlorostyrene and divinyl benzene; and 3-phenylpropylene, 4-phenylpropylene and α-methyl styrene, or the like, may be coexisted in the reaction system to carry out the polymerization.

In the process for producing an olefin polymer according to the present invention, at least one kind of the monomer is ethylene or propylene. When two or more kinds of monomers are used, it is preferable that the amount of ethylene, propylene, or ethylene+propylene is 50% by mole or more, based on the total amount of monomers. Specifically, the monomer can be preferably used for producing an ethylene/propylene copolymer (EPR), a propylene/ethylene copolymer (PER), a propylene/ethylene random copolymer (RCP), a propylene/ethylene impact copolymer (ICP), a propylene/butene copolymer (PBR), apropylene/ethylene/butene copolymer (PEBR), and the like.

Hereinafter, the present invention will be explained in detail with reference to Examples.

[Measurement Method for Properties]

Ethylene Content in Polymer

By the use of Fourier transform infrared spectrophotometer FT/IR-610 manufactured by JASCO Corporation, the area in the vicinity of the rocking vibration of 1155 cm$^{-1}$ based on a methyl group of propylene and the absorbance in the vicinity of the overtone absorption of 4325 cm$^{-1}$ due to a C—H stretching vibration were determined, and by using the obtained ratio, the ethylene content in the polymer was calculated from the standard curve (prepared by using the standard sample which is standardized by $^{13}$C-NMR).

Intrinsic Viscosity ([η])

The specific viscosity ηsp was determined in decalin at 135° C. using an automatic viscosity measuring apparatus VMR-053PC manufactured by Rigo Co. Ltd. and improved version of Ubbelohde capillary viscometer, to calculate the intrinsic viscosity according to the following equation:

[η]=η$_{sp}$/{C(1+K·η$_{sp}$)}<C: solution concentration [g/dl], K: constant number>

Weight Average Molecular Weight (Mw) and Number Average Molecular Weight (Mn)

The measurement was carried out by transferring 500 μl of a sample solution with 0.1 wt % concentration at a flow rate of 1.0 ml/min using Alliance GPC 2000 manufactured by Waters Co., Ltd. The standard polystyrene made by Tosoh Corporation was used and calculated as the calibrated molecular weight of each polymer.

Separating Column: TSKgel GMH6-HT and TSKgel GMH6-HTL (each column having an inner diameter of 7.5 mm and a length of 300 mm)

Column temperature: 140° C.

Mobile phase: o-Dichlorobenzene

Detector: Differential refractometer

EXAMPLES

Hereinafter, the present invention will be further explained in detail with reference to Examples, but the present invention is not limited thereto.

In addition, the structure of compound obtained in Synthesis Examples was determined with the use of 270 MHz $^{1}$H-NMR (GSH-270 manufactured by JEOL Ltd), FD-mass analysis (SX-102A manufactured by JEOL Ltd), and the like.

Example 1

1,1,3,6,8,8-hexamethyl-1H,8H-dicyclopenta[b,h] fluorene

To a 300-ml three-neck flask, 25.8 g of anhydrous aluminum chloride, 5.18 g of fluorene, and 200 ml of carbon disulfide were charged under nitrogen atmosphere. 6.18 g of mesityl oxide was added dropwise thereto over 15 minutes in a water bath, and the mixture was stirred for 10 hours under reflux. After standing to cool, 100 ml of water was added thereto, and the organic layer was separated. The aqueous layer was extracted with 300 ml of hexane, and the separated organic layer was combined, and washed with water and a saturated aqueous solution of sodium chloride. After the solution was dried over magnesium sulfate, the solvent was distilled off, and the obtained product was purified by column chromatography, and recrystallized with a mixed solvent of ethanol/hexane. The yield was 1.14 g. Identification was performed by $^{1}$H-NMR spectrum. The measurement results are shown as follows.

$^{1}$H-NMR (270 MHz, CDCl$_{3}$, TMS standard): δ 7.62 (s, 2H), δ 7.43 (s, 2H), δ 6.03 (s, 2H), δ 3.89 (s, 2H), δ 2.19 (s, 6H), δ 1.33 (s, 12H)

Example 2

(Phenyl)(methyl)methylene(3-tert-butyl-5-methylcyclopentadienyl)(1,1,3,6,8,8-hexamethyl-1H,8H-dicyclopenta[b,h]fluorenyl)zirconium dichloride (1) Synthesis of 3-tert-butyl-6-phenyl-1,6-dimethyl-fulvene To a 100-ml three-neck flask, 1.50 g of potassium hydroxide pulverized in mortar, 0.91 g of 18-crown-6 and 45 ml of THF were charged under nitrogen atmosphere. 2.70 g of t-butyl-methylcyclopentadiene was added dropwise thereto over 10 minutes in a water bath, and the mixture was stirred for 3 hours. The solution was added with 11.33 g of acetophenone dropwise over 10 minutes, and the mixture was stirred for 22 hours. The reaction solution was poured into 100 ml of 2N hydrochloric acid. The organic layer was separated, and the aqueous layer was extracted with 200 ml of hexane. The separated organic layers were combined, and washed with a saturated aqueous solution of sodium hydrogen carbonate, water, and a saturated aqueous solution of sodium chloride. After the solution was dried over magnesium sulfate, the solvent was distilled off, and the obtained product was purified by column chromatography. The yield was 1.98 g. Identification was performed by $^{1}$H-NMR spectrum. The measurement result is shown as follows. The result of the $^{1}$H-NMR spectrum proved that the obtained compounds are a mixture of the isomers.

$^{1}$H-NMR (270 MHz, CDCl$_{3}$, TMS standard): δ 7.37-7.30 (m, 4H), 7.24-7.20 (m, 1H), 6.33+5.56 (m+m, 1H), 6.17+6.11 (d+d, 1H), 2.50+2.41 (s+s, 3H), 2.34+1.36 (s+s, 3H), 1.19+1.01 (s+s, 9H)

(2) Synthesis of (phenyl)(methyl)methylene(3-tert-butyl-5-methylcyclopentadienyl)(1,1,3,6,8,8-hexamethyl-1H,8H-dicyclopenta[b,h]fluorenyl)

To a 100-ml three-neck flask, 1.71 g of 1,1,3,6,8,8-hexamethyl-1H,8H-dicyclopenta[b,h]fluorene and 40 ml of dehydrated ether were charged. 3.5 ml (5.4 mmol) of 1.54 M n-butyllithium hexane solution was added dropwise thereto over 3 minutes in an ice/acetone bath. The solution was stirred for 21 hours while gradually elevating the temperature thereof to room temperature. Thereto, diethyl ether solution of 1.41 g (5.92 mmol) of 3-t-butyl-6-phenyl-1,6-dimethylfulvene was added over 10 minutes. After stirring for 7 days under reflux, the reaction solution was poured into 100 ml of 1 N hydrochloric acid. The organic layer was separated, and the aqueous layer was extracted twice with 75 ml of hexane. The obtained organic layers were combined, washed once with a saturated aqueous solution of sodium hydrogen carbonate, twice with water, and once with saturated brine, and dried over magnesium sulfate. The solvent was distilled off. The obtained solid was purified by column chromatography and washed with methanol. The yield was 0.70 g. Identification was performed by FD-MS spectrum. The measurement result is shown as follows.

FD-MS: m/Z=564(M+)

(3) Synthesis of (phenyl)(methyl)methylene(3-tert-butyl-5-methylcyclopentadienyl)(1,1,3,6,8,8-hexamethyl-1H,8H-dicyclopenta[b,h]fluorenyl)zirconium dichloride To a 30-ml Schlenk tube, 0.691 g of (phenyl)(methyl) methylene(3-tert-butyl-5-methylcyclopentadienyl)(1,1,3,6, 8,8-hexamethyl-1H,8H-dicyclopenta[b,h]fluorenyl) and 15 ml of ether were charged under nitrogen atmosphere. 1.75 ml (2.70 mmol) of a 1.54 M n-BuLi hexane solution was added thereto in an ice/acetone bath, and then the mixture was stirred for 10 minutes. The solution was stirred at room temperature for 24 hours. After cooling the solution in an ice/acetone bath, 0.439 g (1.88 mmol) of zirconium tetrachloride was added thereto, and the mixture was stirred for 19 hours while the temperature thereof was gradually elevated back to room temperature. After the solvent was distilled off, the solubles were extracted with hexane. The solvent was distilled off, and the obtained product was recrystallized with ether. Obtained crystals were washed with pentane. The yield was 52 mg. Identification was performed by $^1$H-NMR spectrum and FD-MS. The measurement results are shown as follows.

$^1$H-NMR spectrum (270 MHz, CDCl$_3$, TMS standard): δ 7.94-7.90 (m, 1H), 7.87 (s, 1H), 7.85 (s, 1H), 7.82 (s, 1H), 7.76-7.73 (m, 1H), 7.65-7.50 (m, 1H), 7.45-4.38 (m, 2H), 6.09 (d, 1H), 6.03 (d, 1H), 5.90 (d, 1H), 5.90 (d, 1H), 5.87 (d, 1H), 5.54 (d, 1H), 2.78 (s, 3H), 2.42 (s, 3H), 2.20 (d, 3H), 2.16 (d, 3H), 1.53 (s, 3H), 1.35 (s, 6H), 1.21 (s, 1H), 1.01 (s, 9H), 0.96 (s, 3H), 0.86 (s, 3H), FD-MS: m/Z=724 (M+)

Example 3

Preparation of Supported Catalyst

To a 100-ml three-neck flask, which had been thoroughly purged with nitrogen, and equipped with a stirring rod, 1.00 g of silica-supported methylaluminoxane (Al=14.6 wt %) was added. 10 ml of dehydrated toluene was added thereto at room temperature, 20 ml of a toluene solution of 21.0 mg of the (phenyl)(methyl)methylene(3-tert-butyl-5-methylcyclopentadienyl)(1,1,3,6,8,8-hexamethyl-1H,8H-dicyclopenta[b,h] fluorenyl)zirconium dichloride synthesized by the above-mentioned Example 2 was added as a transition metal compound under stirring, and the mixture was stirred for 1 hour. The obtained slurry was filtered, and powder on the filter was washed once with 10 ml of dehydrated toluene, and subsequently washed three times with 10 ml of dehydrated hexane. The washed powder was dried under reduced pressure for 2 hours to obtain 0.934 g of powder. The obtained powder was mixed with 8.41 g of a mineral oil to obtain a 10.0 wt % slurry.

Example 4

Propylene/Ethylene Copolymerization

To an SUS-made autoclave having an internal volume of 2000 ml, which had been thoroughly purged with nitrogen, 300 g of liquid propylene was charged, and then heated to 55° C. under sufficient stirring. The inside of the autoclave was pressurized with ethylene gas to 30 kg/cm$^2$G. Subsequently, to a pot for charging a catalyst having an internal volume of 30 ml, which had been thoroughly purged with nitrogen, attached on the autoclave, a mixture solution of 4 ml of dehydrated hexane and 1 ml of a hexane solution (Al=1.0 M) of triisobutylaluminum was added, and charged to the autoclave while pressurizing it with nitrogen. Next, to the pot for charging catalyst, the mixture of 344 mg of the supported catalyst slurry prepared in the above-mentioned Example 3 and 1.0 mmol of a hexane solution (Al=1.0 M) of triisobutylaluminum was added, and charged to the autoclave while pressurizing it with nitrogen to initiate the polymerization. After carrying out the polymerization for 3 minutes, a small amount of methanol was added to terminate the polymerization. The polymer was added to an excessive amount of methanol added with hydrochloric acid to carry out deashing. The resultant polymer was separated by filtration, and then dried at 80° C. for 10 hours under reduced pressure to obtain 16.7 g of a polymer. The polymerization activity was 342 kg-Polymer/mmol-Zr·hr. The results of polymer analysis showed an ethylene content of the polymer=30% by mole, [η]=2.22 dl/g, Mw=238,000, an Mw/Mn=2.0.

Example 5

Propylene/Ethylene Copolymerization

The polymerization was carried out under the same condition as in the above Example 4, except that 347 mg of the supported catalyst slurry prepared in the above-mentioned Example 3 was used, the inside of the autoclave was pressurized with ethylene gas to 35 kg/cm$^2$G, and that the polymerization was carried out for 4 minutes. The obtained polymer was 50.9 g and the polymerization activity was 773 kg-Polymer/mmol-Zr·hr. The results of polymer analysis showed an ethylene content of the polymer=47% by mole, [η]=2.55 dl/g, Mw=250,000, and Mw/Mn=2.0.

Example 6

Propylene/Ethylene Copolymerization

The polymerization was carried out under the same condition as in the above Example 4, except that 199 mg of the supported catalyst slurry prepared in the above-mentioned Example 3 was used, the inside of the autoclave was pressurized with ethylene gas to 40 kg/cm$^2$G, and that the polymerization was carried out for 4 minutes. The obtained polymer was 24.3 g, and the polymerization activity was 734 kg-Polymer/mmol-Zr·hr. The results of polymer analysis showed an ethylene content of the polymer=60% by mole, [η]=3.04 dl/g, Mw=305,000, and Mw/Mn=2.1.

Example 7

Propylene Bulk Polymerization

To a 50-ml side-arm flask which had been thoroughly purged with nitrogen, and equipped with a magnetic stirrer, 1.02 g of the supported catalyst slurry prepared in the above-mentioned Example 3, 1.0 mmol of a hexane solution (Al=11.0M) of triisobutylaluminum, and 5.0 ml of dehydrated hexane were added. The resultant mixture was introduced to an SUS-made autoclave having an internal volume of 2000 ml, which had been thoroughly purged with nitrogen. Thereafter, 500 g of liquid propylene was charged thereto. After the polymerization was carried out at 70° C. for 40 minutes, the autoclave was cooled, and propylene was purged to terminate the polymerization. The polymer was dried under reduced pressure at 80° C. for 10 hours. The obtained polymer was 248.9 g of the isotactic polypropylene and the polymerization activity was 128.6 kg-PP/mmol-Zr·hr. The results of polymer analysis showed [η]=3.77 dl/g, Mw=606,000, Mw/Mn=2.9, and Tm=147.4° C.

Example 8

Propylene Bulk Polymerization

The polymerization was carried out under the same condition as in the above Example 7, except that 0.340 g of the supported catalyst slurry prepared in the above-mentioned Example 3 was used, and that 0.30 Nl of hydrogen was added after charging 500 g of liquid propylene. The obtained polymer was 328.9 g of the isotactic polypropylene and the polymerization activity was 510.0 kg-PP/mmol-Zr-hr. The results of polymer analysis showed [η]=2.18 dl/g, Mw=261,000, Mw/Mn=2.7, and Tm=150.1° C.

Example 9

Propylene Bulk Polymerization

The polymerization was carried out under the same condition as in the above Example 7, except that 0.201 g of the supported catalyst slurry prepared in the above-mentioned Example 3 was used, and that 0.60 Nl of hydrogen was added after charging 500 g of liquid propylene. The obtained polymer was 255.0 g of the isotactic polypropylene and the polymerization activity was 670.2 kg-PP/mmol-Zr-hr. The results of polymer analysis showed [η]=1.16 dl/g, Mw=121,000, Mw/Mn=2.3, and Tm=150.3° C.

Example 10 di-p-Tolylmethylene(cyclopentadienyl(1,1,3,6,8,8-hexamethyl-1H,8H-dicyclopenta[b,h]fluorenyl)zirconium dichloride (1) Synthesis of 6,6-di-p-tolylfulvene To a 200-ml two-neck flask equipped with a magnetic stirrer, a three-way cock, 6.72 g (31.9 mmol) of 4,4'-dimethylbenzophenone, and 30 ml of tetrahydrofuran were charged under nitrogen atmosphere. 19 ml (38 mmol) of a 2.0 mol/l sodium cyclopentadienyl/tetrahydrofuran solution was gradually added thereto, while cooling it in an ice water bath, and the mixture was stirred at room temperature for 6 days. 100 ml of 1 N hydrochloric acid was gradually added thereto, while cooling it in an ice water bath and 100 ml of diethyl ether was added. The organic layer was separated, and washed twice with 100 ml of water, and once with 100 ml of saturated solution of salt. After the solution was dried over magnesium sulfate, the solvent was distilled off, and the obtained product was purified by column chromatography. The production quantity was 6.15 g, and the yield was 74.5%. Identification was performed by $^1$H NMR spectrum. The measurement result is shown as follows.

$^1$H-NMR (270 MHz, CDCl$_3$, TMS standard): d 2.39 (s, 6H), 6.2-6.3 (m, 2H), 6.5-6.6 (m, 2H), 7.1-7.2 (m, 2H)

(2) Synthesis of (1,1,3,6,8,8-hexamethyl-1H,8H-dicyclopenta[b,h]fluorenyl)(cyclopentadienyl)di-p-tolylmethane To a 200-ml two-neck flask equipped with a magnetic stirrer, a three-way cock and a 50 ml dropping funnel, 749 mg (2.29 mmol) of 1,1,3,6,8,8-hexamethyl-1H,8H-dicyclopenta[b,h]fluorene and 30 ml of tetrahydrofuran were charged under nitrogen atmosphere. 1.56 ml (2.43 mmol) of 1.56 mol/l n-butyllithium/hexane solution was gradually added thereto, while cooling it in an ice water bath, and the mixture was stirred at room temperature for 6.5 hours. 718 mg (2.78 mmol) of 6,6-di-p-tolylfulvene dissolved in 30 ml of tetrahydrofuran in advance was gradually added thereto over 20 minutes using the dropping funnel, while cooling it in a methanol/dry ice bath. The temperature of the reaction solution was gradually elevated back to room temperature, and the solution was stirred at room temperature for 20 hours. 50 ml of 1 N hydrochloric acid was gradually added thereto, and 50 ml of diethyl ether was further added to the mixture. The organic layer was separated, washed twice with 50 ml of water, once with 50 ml of saturated solution of salt. After the solution was dried over magnesium sulfate, the solvent was distilled off, and the obtained product was purified by column chromatography. The production quantity was 397 mg (0.679 mmol), and the yield was 29.6%. Identification was performed by $^1$H-NMR spectrum and FD-MS spectrum. The measurement results are shown as follows.

$^1$H-NMR spectrum (270 MHz, CDCl$_3$, TMS standard): 0.8-1.4 (m, 12H), 1.8-2.2 (m, 6H), 2.2-2.3 (m, 6H), 2.8-3.1 (br, 1H), 5.33 (s, 1H), 5.9-6.0 (m, 2H), 6.0-6.6 (br, 4H), 6.7-7.5 (br, 12H)

FD-MS: M/z 584 (M$^+$)

(2) Synthesis of di-p-tolylmethylene(cyclopentadienyl)(1,1,3,6,8,8-hexamethyl-1H,8H-dicyclopenta[b,h]fluorenyl)zirconium dichloride To a 100-ml Girudarl flask equipped with a three-way cock a magnetic stirrer, 376 mg (0.643 mmol) of (1,1,3,6,8,8-hexamethyl-1H,8H-dicyclopenta[b,h]fluorenyl)(cyclopentadienyl)di-p-tolylmethane, and 40 ml of diethyl ether were charged under nitrogen atmosphere. 0.86 ml (1.3 mmol) of a 1.56 mol/l n-butyllithium/hexane solution was gradually added thereto, while cooling it in an ice water bath, and the mixture was stirred at room temperature for 20 hours under nitrogen atmosphere. 0.260 g (0.688 mmol) of zirconium tetrachloride.tetrahydrofuran complex (1:2) was added thereto, while cooling it in a methanol/dry ice bath. The temperature of the reaction solution was gradually elevated back to room temperature, and the solution was stirred at room temperature for 17 hours. The solid obtained by distilling off the solvent under reduced pressure was extracted with hexane, and the solvent of the obtained solution was distilled off under reduced pressure. The obtained product was washed with pentane, and then extracted with dichloromethane. The solvent of the obtained solution was distilled off under reduced pressure to obtain a title compound. The production quantity was 149 mg (0.200 mmol), and the yield was 31.1%. Identification was performed by $^1$H-NMR spectrum and FD-MS spectrum. The measurement results are shown as follows.

$^1$H-NMR spectrum (270 MHz, CDCl$_3$, TMS standard): 0.94 (s, 6H), 1.04 (s, 6H), 2.17 (d, 6H), 2.35 (s, 6H), 5.68 (t, 2H), 5.95 (d, 2H), 6.10 (s, Ar (Flu), 2H), 6.28 (t, 2H), 7.1-7.3 (m, 4H), 7.8-7.9 (m, 4H), 7.91 (s, 2H)

FD-MS: M/z 744 (M$^+$)

Example 11

Preparation of Supported Catalyst

To a 100-ml three-neck flask, which had been thoroughly purged with nitrogen, a stirring rod was equipped and 0.989 g of silica-supported methylaluminoxane (Al=19.3 wt %) and 42 ml of toluene were added. Thereto, a solution prepared by dissolving 20.2 mg (0.0271 mmol) of di-p-tolylmethylene (cyclopentadienyl(1,1,3,6,8,8-hexamethyl-1H,8H-dicyclopenta[b,h]fluorenyl)zirconium dichloride as synthesized by the above-mentioned Example 10 in 8.0 ml of toluene, was gradually added as a transition metal compound, and the mixture was stirred at room temperature for 1 hour. After stopping stirring the solution, the solution was left to stand, and then the supernatant was removed by decantation. Thereafter, the operation of adding 45 ml of heptane and stirring the mixture, settling the mixture to stand, and removing the supernatant by a decantation, was performed three times. Subsequently, heptane was added to obtain 50 ml of a slurry. Thereto, 2.0 ml (Al=2.0 mmol) of an n-decane solution of triisobutylaluminum was added while stirring, ethylene was blown into the slurry, and the polymerization was carried out at 20° C. for 34 minutes. After stopping supplying ethylene and stirring the mixture, the solution was settled, and the supernatant was removed by a decantation. Thereafter, the operation of adding 45 ml of heptane and stirring the mixture, leaving the mixture to stand, and removing the supernatant by a decantation, was performed three times. Subsequently, heptane was added to obtain a total amount of 100 ml of a slurry. From this, a heptane slurry of the supported catalyst of the previous polymerization was obtained.

Example 12

Ethylene Homopolymer

To an SUS-made autoclave having an internal volume of 1 liter, which had been thoroughly purged with nitrogen, 500 ml of purified heptane was added, and ethylene was passed therethrough to saturate a liquid phase and a gas phase with ethylene. Subsequently, using the hydrogen-ethylene mixed gas (hydrogen concentration: 0.99 vol %), the internal system was substituted, and then 0.25 mmol of triisobutylaluminum, and 5.0 ml of the supported catalyst slurry prepared in the Example 11 were charged thereto in the order. The temperature of the system was elevated to 80° C., and the polymerization was carried out at 0.78 MPa·G for 1 hour. The obtained polymer was dried under vacuum for 10 hours to obtain 56.7 g of an ethylene polymer. The polymerization activity was 1120 g-PE/g-cat·h. The [η] of the obtained ethylene polymer was 0.88 dl/g.

Example 13

Ethylene/1-Hexene Copolymer

To an SUS-made autoclave having an internal volume of 1 liter, which had been thoroughly purged with nitrogen, 500 ml of purified heptane was added, and ethylene was passed therethrough to saturate a liquid phase and a gas phase with ethylene. Subsequently, 0.25 mmol of triisobutylaluminum, and 3.0 ml of 1-hexene, 1.4 ml of the supported catalyst slurry prepared in the Example 11 were charged in the order. The temperature of the system was elevated to 80° C., and the polymerization was carried out at 0.78 MPa·G for 45 minutes. The obtained polymer was dried under vacuum for 10 hours to obtain 74.7 g of an ethylene/1-hexene copolymer. The polymerization activity was 7060 g-PE/g-cat·h. The density of the obtained ethylene polymer was 0.946 g/cm$^3$.

Comparative Example 1

Preparation of Supported Catalyst

To a 100-ml three-neck flask, which had been thoroughly purged with nitrogen, and equipped with a stirring rod, 1.01 g of silica-supported methylaluminoxane (Al=14.6 wt %) was added. Thereto, 10 ml of dehydrated toluene was added at room temperature, 20 ml of a toluene solution of 20.6 mg of the isopropylidene(3-tert-butyl-5-methylcyclopentadienyl)(fluorenyl)zirconium dichloride synthesized in accordance with WO01/27124 was added as a transition metal compound under stirring, and the mixture was stirred for 1 hour. The obtained slurry was filtered, and powders on the filter were washed once with 10 ml of dehydrated toluene, and then washed three times with 10 ml of dehydrated hexane. The washed powders were dried under reduced pressure for 2 hours to obtain 0.929 g of powders. The obtained powders were mixed with 8.36 g of a mineral oil to obtain a 10.0 wt % slurry.

Comparative Example 2

Propylene/Ethylene Copolymerization

To an SUS-made autoclave having an internal volume of 2000 ml, which had been thoroughly purged with nitrogen, 300 g of liquid propylene was charged, then heated to 55° C. under sufficient stirring, and the inside of the autoclave was pressurized with ethylene gas to 35 kg/cm$^2$G. Subsequently, to a pot for charging a catalyst having an internal volume of 30 ml, which had been thoroughly purged with nitrogen, attached on the autoclave, a mixed solution of 4 ml of dehydrated hexane and 1 ml of hexane solution (Al=1.0 M) of triisobutylaluminum was added, and charged to the autoclave while pressurizing it with nitrogen. Next, to the pot for charging a catalyst, a mixture of 170 mg of the supported catalyst slurry prepared in the above-mentioned Comparative Example 1 and 1.0 mmol of a hexane solution (Al=1.0 M) of triisobutylaluminum was added, and charged to the autoclave while pressurizing it with nitrogen to initiate the polymerization. After carrying out the polymerization for 5 minutes, a small amount of methanol was added thereto to terminate the polymerization. The polymer was added to an excessive amount of methanol added with hydrochloric acid to carry out deashing. The resultant polymer was separated by filtration, and then dried at 80° C. for 10 hours under reduced pressure to obtain 19.6 g of a polymer. The polymerization activity was 174 kg-Polymer/mmol-Zr·hr. The results of polymer analysis showed an ethylene content of the polymer=39% by mole, [η]=1.00 dl/g, Mw=74,000, and Mw/Mn=2.0.

Comparative Example 3

Propylene Bulk Polymerization

To a 50-ml side-arm flask, which had been thoroughly purged with nitrogen, and equipped with a magnetic stirrer, 0.262 g of the supported catalyst slurry prepared in the above-mentioned Comparative Example 1, 1.0 mmol of a hexane solution (Al=11.0M) of triisobutylaluminum and 5.0 ml of dehydrated hexane were added. The resultant mixture was introduced to an SUS-made autoclave having an internal volume of 2000 ml, which had been thoroughly purged with nitrogen. Thereafter, 500 g of liquid propylene was charged thereto, and then 0.30 Nl of hydrogen was added. After the polymerization was carried out at 70° C. for 40 minutes, the autoclave was cooled, and propylene was purged to terminate the polymerization. The polymer was dried under reduced pressure at 80° C. for 10 hours. The obtained polymer was 171.1 g of isotactic polypropylene, and the polymerization activity was 246 kg-PP/mmol-Zr·hr. The results of polymer analysis showed [η]=1.67 dl/g, Mw=198,000, Mw/Mn=2.2, and Tm=142.3° C.

INDUSTRIAL APPLICABILITY

The fluorene compound in which a carbon-carbon unsaturated bond is substituted at the 3- and 6-positions thereof, and the useful and novel transition metal compound which has a ligand containing a fluorenyl group corresponding to the fluorene compound, are novel and useful as a catalyst component for olefin polymerization. The catalyst for olefin polymerization containing the transition metal compound exhibits extremely high activity, which accordingly provides a process for more economically producing an olefin polymer.

The invention claimed is:

1. A transition metal compound represented by the following general formula [III]:

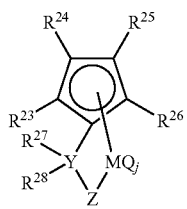

[III]

wherein $R^{23}$, $R^{24}$, $R^{25}$, $R^{26}$, $R^{27}$, and $R^{28}$ are each independently selected from hydrogen, a hydrocarbon group, a silicon-containing group, a sulfur-containing group, an oxygen-containing group, a nitrogen-containing group, and a halogen-containing group, adjacent substituents of $R^{23}$ to $R^{28}$ are optionally bonded to each other to form a ring, M is a Group 4 transition metal, Y is carbon atom, Q is selected from halogen, a hydrocarbon group, an anionic ligand and a neutral ligand capable of coordinating with a lone electron pair, which is selected in the same combination or different combination, j is an integer of 1 to 4, and Z is selected from a fluorenylidene group having a free valency of divalence, which is derived by removing $R^1$ and $R^2$ from the fluorene derivative represented by the general formula [I]

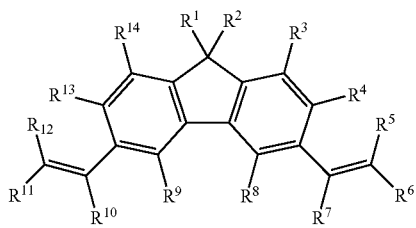

[I]

wherein $R^1$, $R^2$, $R^3$, $R^5$, $R^6$, $R^7$, $R^8$, $R^9$, $R^{10}$, $R^{11}$, $R^{12}$, and $R^{14}$ are each independently selected from hydrogen, a hydrocarbon group and a silicon-containing group, $R^4$ and $R^{13}$ are each independently selected from hydrogen, a hydrocarbon group, a silicon-containing group, a sulfur-containing group, an oxygen-containing group, a nitrogen-containing group, and a halogen-containing group, adjacent substituents of $R^1$ to $R^{14}$ are optionally bonded to each other to form a ring, $R^4$ and $R^5$ are optionally joined together to form Ra which is a divalent substituent, $R^{12}$ and $R^{13}$ are optionally joined together to form Rb which is a divalent substituent, wherein Ra and Rb are each a divalent substituent other than a vinylene group, which is selected from a hydrocarbon group, a silicon-containing group, a sulfur-containing group, an oxygen-containing group, a nitrogen-containing group, and a halogen-containing group; or a fluorenylidene group having a free valency of divalence, which is derived by removing two hydrogen atoms at the 10-position of the fluorene derivative of general formula [II]:

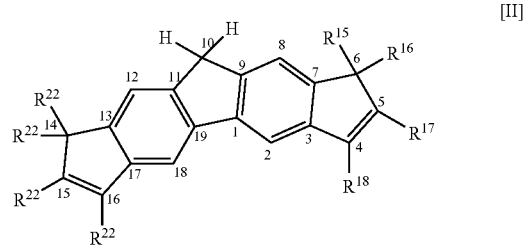

[II]

wherein $R^{15}$, $R^{16}$, $R^{17}$, $R^{18}$, $R^{19}$, $R^{20}$, $R^{21}$, and $R^{22}$ are each independently selected from hydrogen, a hydrocarbon group, a silicon-containing group, a sulfur-containing group, an oxygen-containing group, a nitrogen-containing group, and a halogen-containing group; or wherein $R^{15}$, $R^{16}$, $R^{18}$, $R^{19}$, $R^{21}$, and $R^{22}$ are each a methyl group, and $R^{17}$ and $R^{20}$ are each hydrogen.

2. The transition metal compound according to claim 1, wherein $R^{24}$ and $R^{26}$ in the above general formula [III] are each hydrogen.

3. The transition metal compound according to claim 1, wherein $R^1$ and $R^2$ in the general formula [I] are each hydrogen.

4. The transition metal compound according to claim 1, wherein $R^1$, $R^2$, $R^3$, $R^8$, $R^9$, and $R^{14}$ in the general formula [I] are each hydrogen.

5. The transition metal compound according to claim 1, wherein in the general formula [I], $R^1$, $R^2$, $R^3$, $R^8$, $R^9$, and $R^{14}$ are each hydrogen and $R^4$ and $R^5$, and/or $R^{12}$ and $R^{13}$ are bonded to each other to form a ring.

6. The transition metal compound according to claim 1, wherein in the general formula [I], $R^1$, $R^2$, $R^3$, $R^8$, $R^9$, and $R^{14}$ are each hydrogen, and $R^4$ and $R^5$ and/or $R^{12}$ and $R^{13}$ are bonded to each other to form a 5- or 6-membered ring.

* * * * *